(12) United States Patent
Tanaka et al.

(10) Patent No.: US 10,760,116 B2
(45) Date of Patent: Sep. 1, 2020

(54) ANALYSIS KIT, ANALYZER, AND METHODS FOR ANALYZING TEMPLATE NUCLEIC ACID OR TARGET SUBSTANCE

(71) Applicant: KABUSHIKI KAISHA DNAFORM, Yokohama-shi, Kanagawa (JP)

(72) Inventors: Yuji Tanaka, Saitama (JP); Yoshihide Hayashizaki, Saitama (JP); Koichiro Tsujimaru, Kanagawa (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 269 days.

(21) Appl. No.: 15/755,898

(22) PCT Filed: Aug. 26, 2016

(86) PCT No.: PCT/JP2016/074976
§ 371 (c)(1),
(2) Date: Feb. 27, 2018

(87) PCT Pub. No.: WO2017/038682
PCT Pub. Date: Mar. 9, 2017

(65) Prior Publication Data
US 2019/0032108 A1   Jan. 31, 2019

(30) Foreign Application Priority Data

Aug. 28, 2015 (JP) ................................ 2015-169833
May 13, 2016 (JP) ................................ 2016-096998

(51) Int. Cl.
| | |
|---|---|
| C12P 19/34 | (2006.01) |
| C12Q 1/682 | (2018.01) |
| C12Q 1/68 | (2018.01) |
| C12M 1/00 | (2006.01) |
| G01N 21/64 | (2006.01) |

(Continued)

(52) U.S. Cl.
CPC .............. *C12Q 1/682* (2013.01); *C12M 1/00* (2013.01); *C12Q 1/68* (2013.01); *C12Q 1/6818* (2013.01); *C12Q 1/6851* (2013.01); *C12Q 1/6876* (2013.01); *G01N 21/64* (2013.01); *G01N 21/6428* (2013.01); *C12N 15/09* (2013.01); *C12Q 2600/16* (2013.01); *G01N 2021/6432* (2013.01)

(58) Field of Classification Search
CPC ........ C12Q 2563/107; C12Q 2563/159; C12Q 1/6818; C12Q 1/682; C12Q 1/68; C12Q 1/6876; C12Q 2600/16; G01N 21/6428; G01N 21/64; G01N 2021/6432; C12M 1/00; C12N 15/09
See application file for complete search history.

(56) References Cited

U.S. PATENT DOCUMENTS

2008/0227104 A1   9/2008   Hayashizaki et al.
2010/0092971 A1   4/2010   Okamoto et al.
(Continued)

FOREIGN PATENT DOCUMENTS

EP   2 873 731       5/2015
JP   2009-171935     8/2009
(Continued)

OTHER PUBLICATIONS

Applied Biosystems, QuantStudio 12K Flex real-time PCR system, pp. 1-19 (Year: 2012).*

(Continued)

*Primary Examiner* — Cynthia B Wilder
(74) *Attorney, Agent, or Firm* — Hamre, Schumann, Mueller & Larson, P.C.

(57) ABSTRACT

The present invention provides a method for analyzing a template nucleic acid, a method for analyzing a target substance, an analysis kit for a template nucleic acid or a target substance, and an analyzer for a template nucleic acid or a target substance, which are excellent in accuracy. The method for analyzing a template nucleic acid of the present invention includes the steps of: fractionating a sample containing a template nucleic acid into a plurality of template nucleic acid fractions; amplifying a target sequence and its complementary sequence in the template nucleic acid with respect to each of the plurality of template nucleic acid fractions in the presence of a nucleic acid amplification reagent; detecting generation or quenching of a signal that shows an amplification of the target sequence or the complementary sequence with respect to each of the plurality of template nucleic acid fractions after the amplification step; and discriminating a template nucleic acid fraction in which the generation or quenching of a signal that shows the amplification has been detected among the plurality of template nucleic acid fractions as an amplified fraction in which the target sequence or the complementary sequence has been amplified, wherein the nucleic acid amplification reagent contains a primer set that amplifies the target sequence and the complementary sequence and a signal generating substance that generates or quenches a signal in response to the amplification, and the signal generating substance generates a signal in a state where it is bound sequence-dependently and quenches a signal in a state where it is not bound or quenches a signal in a state where it is bound sequence-dependently and generates a signal in a state where it is not bound, and generation and quenching of a signal are reversible.

17 Claims, 4 Drawing Sheets
Specification includes a Sequence Listing.

(51) Int. Cl.
  *C12Q 1/6818*  (2018.01)
  *C12Q 1/6851*  (2018.01)
  *C12Q 1/6876*  (2018.01)
  *C12N 15/09*   (2006.01)

(56) References Cited

U.S. PATENT DOCUMENTS

| 2014/0178889 | A1* | 6/2014 | Do .................. C12Q 1/686 |
| | | | 435/6.12 |
| 2015/0152496 | A1 | 6/2015 | Hayashizaki et al. |
| 2015/0203902 | A1 | 7/2015 | Hayashizaki |
| 2015/0275274 | A1 | 10/2015 | Afonina et al. |
| 2017/0145482 | A1* | 5/2017 | Hanami .................. C09B 23/04 |
| 2017/0183717 | A1 | 6/2017 | Afonina et al. |

FOREIGN PATENT DOCUMENTS

| JP | 4370385 | 11/2009 |
| JP | 2013-541347 | 11/2013 |
| JP | 2014-515268 | 6/2014 |
| WO | 2011/142836 | 11/2011 |
| WO | 2014/013954 | 1/2014 |
| WO | 2014/034818 | 3/2014 |
| WO | 2015/152024 | 10/2015 |

OTHER PUBLICATIONS

Mitani et al., "Rapid SNP diagnostics using asymmetric isothermal amplification and a new mismatch-suppression technology", Nature Methods, vol. 4, No. 3, pp. 257-262, 2007.

McDermott G. P. et al., "Multiplexed Target Detection Using DNA-Binding Dye Chemistry in Droplet Digital PCR", Analytical Chemistry, vol. 85, pp. 11619-11627, 2013.

Miotto et al., "Quantification of Circulating miRNAs by Droplet Digital PCR: Comparison of EvaGreen- and TaqMan-Based Chemistries", Cancer Epidemiology, Biomarkers & Prevention, vol. 23, No. 12, pp. 2638-2642, 2014.

"QuantStudio (TM) 3D Digital PCR System", Catalog No. A29154 or A29157, QuantStudio (TM) 3D Digital PCR System Quick Reference, pp. 1-4, Jul. 28, 2015.

"QuantStudio (TM) 12K Flex, Real-time PCR system, All-in-one real-time PCR device", Life technologies Japan Corporation, pp. 1-19, 2012.

Dong et al., "Comparison of four digital PCR platforms for accurate quantification of DNA copy number of a certified plasmid DNA reference material", Scientific Reports, vol. 5, 13174 (11 pages), Aug. 25, 2015.

Hanami et al., "Eprobe Mediated Real-Time PCR Monitoring and Melting Curve Analysis", PLOS One, vol. 8, No. 8, e70942 (12 pages), 2013.

Hindson et al., "High-Throughput Droplet Digital PCR System for Absolute Quantitation of DNA Copy Number", Analytical Chemistry, vol. 83, pp. 8604-8610, 2011.

Partial Supplementary European Search Report for the corresponding European Patent Application No. 16841714.5 dated Feb. 21, 2019, 13 pages.

Rudnitskaya, et al., Microchip Devices for Polymeraze Chain Reaction. P. 1. PCR Main Principles; Design and Materials of Microchips, Scientific Device Engineering, 2008, vol. 18, No. 3, pp. 3-20 with an English Abstract on p. 20.

Borodulin, et al., "Technology and Application of DNA Microarray" Southern Caucasus Region, Earth Sciences, No. 1, 2012, pp. 69-73 with an English Abstract.

Waters, et al., "Multiple Sample PCR Amplification and Electrophoretic Analysis on a Microchip", Analytical Chemistry, 1998, No. 70 (24), pp. 5172-5176.

Office Action issued in corresponding Russian Patent Application No. 2018110790, dated Apr. 7, 2020, 10 pages with translation.

* cited by examiner (A) Analysis method of Example 1

(B) Analysis method of Comparative Example 1

SEQUENCE LISTING

```
<160> NUMBER OF SEQ ID NOS: 16

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1
cgcgggaggt cagcgttcac actagtgacc c                                31

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
accttctata ccctcagaag gtcgggagtt cagggtaaag gt                    42

<210> SEQ ID NO 3
<211> LENGTH: 15
<212> TYPE: DNA
<213> ORGANISM: Artificial Sequence
<220> FEATURE:
<223> OTHER INFORMATION: primer

<400> SEQUENCE: 3
tcgcaggtgc ctgtc                                                  15

<210> SEQ ID NO 4
<211> LENGTH: 12
<212> TYPE: DNA
<213> ORGANISM: Artificial Sequence
<220> FEATURE:
<223> OTHER INFORMATION: primer

<400> SEQUENCE: 4
ggctgcgggg cc                                                     12
```

```
<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
caatcccgcc cagactac                                                 18

<210> SEQ ID NO 6
<211> LENGTH: 13
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is exciton labelled Thiamine

<400> SEQUENCE: 6
cggggnccgc tgc                                                      13

<210> SEQ ID NO 7
<211> LENGTH: 14
<212> TYPE: DNA
<213> ORGANISM: Artificial Sequence
<220> FEATURE:
<223> OTHER INFORMATION: oligonucleotide

<400> SEQUENCE: 7
ctacgccacc agct                                                     14

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
gagaaagaga aagatacaca                                               20

<210> SEQ ID NO 9
<211> LENGTH: 14
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (12)..(12)
<223> OTHER INFORMATION: n is Thiazole orange labeled thymine

<400> SEQUENCE: 9
agctggtggc gnag                                                     14

<210> SEQ ID NO 10
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (9)..(9)
```

<223> OTHER INFORMATION: n is Thiazole pink labeled thymine

<400> SEQUENCE: 10
tgtgtatcnt tctctttctc                                               20

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
ttccattgcg aatgcacatt cgaagcaac                                     29

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
gcattcgcga aatgataata ccagatcc                                      28

<210> SEQ ID NO 13
<211> LENGTH: 16
<212> TYPE: DNA
<213> ORGANISM: Artificial Sequence
<220> FEATURE:
<223> OTHER INFORMATION: primer

<400> SEQUENCE: 13
accactagat ttccag                                                   16

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
acactagtag agccgggaga                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ctggtgttta tagcaccctt                                               20

<210> SEQ ID NO 16
<211> LENGTH: 16
<212> TYPE: DNA
<213> ORGANISM: Artificial Sequence
<220> FEATURE:
<223> OTHER INFORMATION: primer
<220> FEATURE:

```
<221> NAME/KEY: misc_feature
<222> LOCATION: (6)..(6)
<223> OTHER INFORMATION: n is Thiazole orange labeled thymine

<400> SEQUENCE: 16
accacnagat ttccag                                                    16
```

ANALYSIS KIT, ANALYZER, AND METHODS FOR ANALYZING TEMPLATE NUCLEIC ACID OR TARGET SUBSTANCE

TECHNICAL FIELD

The present invention relates to a method for analyzing a template nucleic acid, a method for analyzing a target substance, an analysis kit for a template nucleic acid or a target substance, and an analyzer for a template nucleic acid or a target substance.

BACKGROUND ART

In the gene analysis, an analysis method utilizing the amplification of a template nucleic acid using a primer and the detection of the amplified product or the detection of the hybridization between the obtained amplified product and a probe is used widely. In the analysis, a probe that detects the amplification reaction of a template nucleic acid, a substance that intercalates into the amplified product, a probe that generates or quenches fluorescence by hybridizing to the amplified product, and the like are used. This method can achieve, for example, the analysis of the presence or absence of a target sequence (qualitative analysis), the analysis of the quantity of the target sequence (quantitative analysis), the typing of a polymorphism site in the target sequence, and the like. The typing can determine, for example, the type of the base (for example, wild type or mutant type) of the polymorphism site, the genotype (homozygous or heterozygous), and the like.

In the gene analysis utilizing the amplification of a template nucleic acid, however, the amplification and the amplification bias of a nucleic acid sequence other than the template nucleic acid sometimes occur, which causes the problems in the specificity, the quantitativity, the sensitivity, and the like. In the medical field, there is a need to detect a small amount of template nucleic acid in a sample. Thus, there is a demand for a gene analysis method with higher accuracy.

BRIEF SUMMARY OF THE INVENTION

Problem to be Solved by the Invention

Hence, the present invention is intended to provide a method for analyzing a template nucleic acid, a method for analyzing a target substance, an analysis kit for a template nucleic acid or a target substance, and an analyzer for a template nucleic acid or a target substance, which have excellent accuracy.

Means for Solving Problem

In order to achieve the above object, the present invention provides a method for analyzing a template nucleic acid, including the steps of: fractionating a sample containing a template nucleic acid into a plurality of template nucleic acid fractions; amplifying a target sequence and its complementary sequence in the template nucleic acid with respect to each of the plurality of template nucleic acid fractions in the presence of a nucleic acid amplification reagent; detecting generation or quenching of a signal that shows an amplification of the target sequence or the complementary sequence with respect to each of the plurality of template nucleic acid fractions after the amplification step; and discriminating a template nucleic acid fraction in which the generation or quenching of a signal that shows the amplification has been detected among the plurality of template nucleic acid fractions as an amplified fraction in which the target sequence or the complementary sequence has been amplified, wherein the nucleic acid amplification reagent contains a primer set that amplifies the target sequence and the complementary sequence and a signal generating substance that generates or quenches a signal in response to the amplification, and the signal generating substance generates a signal in a state where it is bound sequence-dependently and quenches a signal in a state where it is not bound or quenches a signal in a state where it is bound sequence-dependently and generates a signal in a state where it is not bound, and generation and quenching of a signal are reversible.

The present invention also provides a method for analyzing a target substance, including the steps of: bringing a sample containing at least one target substance into contact with at least one fluorogenic probe for each target substance in a reaction solution; and detecting the generation or quenching of a signal of the fluorogenic probe in response to binding between the target nucleic acid and the fluorogenic probe.

The present invention also provides an analysis kit for a template nucleic acid or a target substance that executes the analysis method according to the present invention.

The present invention also provides an analyzer for a template nucleic acid or a target substance that executes the analysis method according to the present invention.

Effects of the Invention

According to the present invention, the template nucleic acid can be analyzed accurately.

MODE FOR CARRYING OUT THE INVENTION

Figure 1:
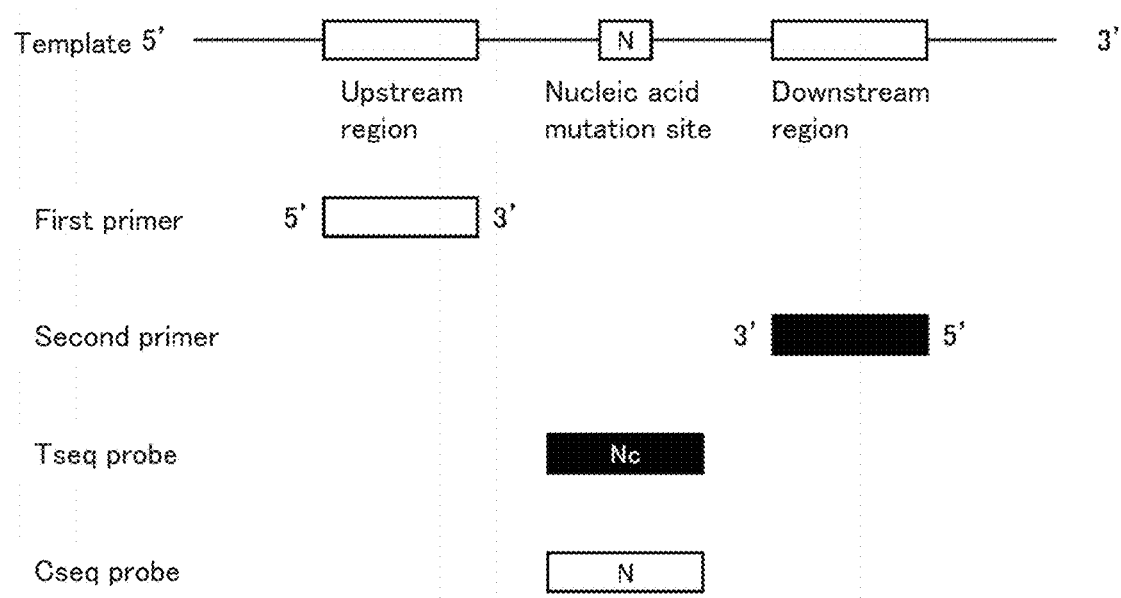
FIG. 1 is a schematic view showing the outline of the design of primers and probes in the present invention.

In the method for analyzing a template nucleic acid of the present invention, for example, the signal generating substance includes a signal generating binding substance including the signal generating substance. The signal generating binding substance is a substance that specifically binds to the target sequence or the complementary sequence. Also, the signal generating binding substance is a substance that generates the signal in a state where it is bound to a target and quenches the signal in a state where it is dissociated from the target or a substance that quenches the signal in a state where it is bound to a target and generates the signal in a state where it is dissociated from the target.

In the method for analyzing a template nucleic acid of the present invention, for example, the signal generating substance includes a fluorogenic probe including the signal generating substance. The fluorogenic probe is a probe that generates the signal in a state where it is bound to a target and quenches the signal in a state where it is dissociated from the target or a probe that quenches the signal in a state where it is bound to a target and generates the signal in a state where it is dissociated from the target.

In method for analyzing a template nucleic acid of the present invention, for example, the fluorogenic probe includes at least two fluorescent atomic groups that exhibit an exciton effect as the signal generating substance per molecule.

In the method for analyzing a template nucleic acid of the present invention, for example, the template nucleic acid is a template nucleic acid in a state where it is bound to a substance that specifically binds to the template nucleic acid. The binding between the template nucleic acid and a substance that specifically binds to the template nucleic acid may be binding based on the specificity of the binding substance or binding not based on the specificity of the binding substance, for example. In the latter case, the binding substance can be, for example, a binding substance labeled with the template nucleic acid.

In the method for analyzing a template nucleic acid of the present invention, for example, the primer set includes a fluorogenic primer including the signal generating substance. The fluorogenic primer is a primer that generates the signal in a state where it is bound to a target and quenches the signal in a state where it is dissociated from the target or a primer that quenches the signal in a state where it is bound to a target and generates the signal in a state where it is dissociated from the target.

In the method for analyzing a template nucleic acid of the present invention, for example, the fluorogenic primer includes at least two fluorescent atomic groups that exhibit an exciton effect as the signal generating substance per molecule.

In the method for analyzing a template nucleic acid of the present invention, for example, a base that includes a pair of fluorescent atomic groups that exhibit an exciton effect has a structure represented by the following formula (16), (16b), (17), or (17b).

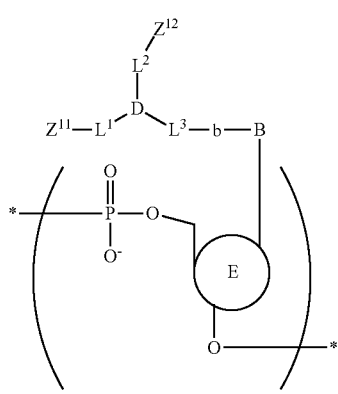

(16)

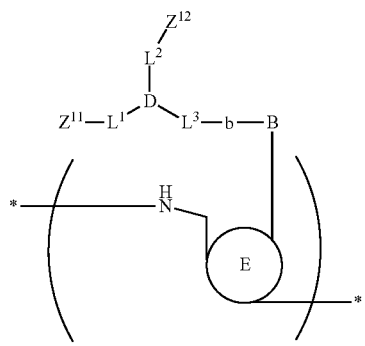

(16b)

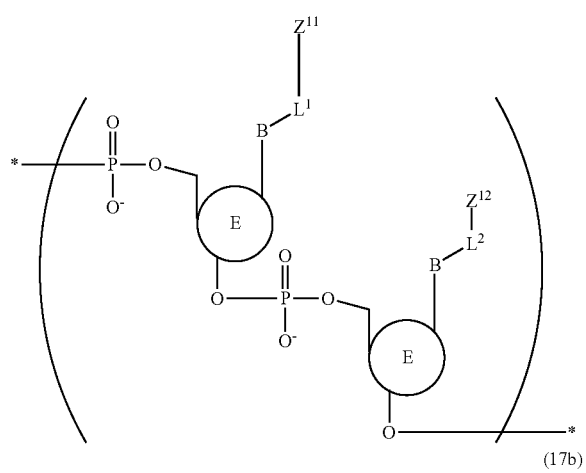

(17)

(17b)

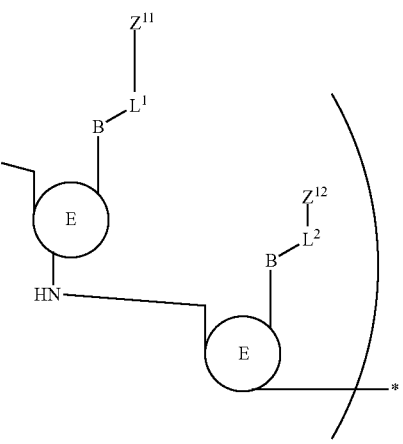

In the method for analyzing a template nucleic acid of the present invention, for example, an amplification method adopted in the amplification step is at least one of an isothermal amplification method and a PCR method.

The method for analyzing a template nucleic acid of the present invention further includes the step of recovering the amplified fraction from the plurality of template nucleic acid fractions after the discrimination step, for example.

The method for analyzing a template nucleic acid of the present invention further includes the step of amplifying the target sequence and the complementary sequence in the template nucleic acid with respect to the amplified fraction after the discrimination step, wherein the amplification step is a second amplification, for example. The amplification method adopted in the second amplification step is at least one of an isothermal amplification method and a PCR method, for example.

In the method for analyzing a template nucleic acid of the present invention, for example, the detection step is conducted by a melting curve analysis.

The method for analyzing a template nucleic acid of the present invention further includes the step of conducting an analysis by a melting curve analysis after the detection step, for example.

In the method for analyzing a template nucleic acid of the present invention, for example, a sample containing the template nucleic acid includes the nucleic acid amplification reagent. In the fractionation step, the sample containing the template nucleic acid and the nucleic acid amplification reagent is fractionated into a plurality of template nucleic acid fractions.

In the method for analyzing a template nucleic acid of the present invention, for example, the fractionation step causes each of the plurality of template nucleic acid fractions to contain the nucleic acid amplification reagent.

In the method for analyzing a template nucleic acid of the present invention, for example, the fractionation step is a step of forming an emulsion from the sample, the template nucleic acid fraction is a drop of the sample dispersed in the emulsion, and the detection step is a step of detecting the generation or quenching of a signal with respect to the drop in the emulsion.

In the detection step of the method for analyzing a template nucleic acid of the present invention, for example, the emulsion is caused to pass through a flow channel, and the generation or quenching of a signal is detected with respect to the drop at a predetermined site of the flow channel when the drop in the emulsion passes through the flow channel.

In the method for analyzing a template nucleic acid of the present invention, for example, the emulsion is a water-in-oil (W/O type) emulsion.

In the method for analyzing a template nucleic acid of the present invention, for example, the fractionation step is a step of fractionating the sample into a plurality of template nucleic acid fractions by dispensing the sample to a chip provided with a plurality of template nucleic acid fraction formation portions on its surface.

In the method for analyzing a template nucleic acid of the present invention, for example, in the chip, a surface of the template nucleic acid fraction formation portion is hydrophilic and a surface of a region excluding the template nucleic acid fraction formation portion is hydrophobic. The fractionation step is a step of fractionating the sample into a plurality of template nucleic acid fractions by applying the sample to the surface of the chip to separate the sample into the template nucleic acid fraction formation portions.

In the method for analyzing a template nucleic acid of the present invention, for example, in the chip, the template nucleic acid fraction formation portion is a dent of the surface of the chip and the region excluding the template nucleic acid fraction formation portion is a non-dent. The fractionation step is a step of fractionating the sample by introducing the sample into the dent of the surface of the chip.

In the method for analyzing a template nucleic acid of the present invention, for example, in the chip, the template nucleic acid fraction formation portion is a dent of the surface of the chip, an inner surface of the template nucleic acid fraction formation portion is hydrophilic, the region excluding the template nucleic acid fraction formation portion is a non-dent, and a surface of the region excluding the template nucleic acid fraction formation portion is hydrophobic.

In the method for analyzing a template nucleic acid of the present invention, for example, the nucleic acid amplification reagent is arranged in the template nucleic acid fraction formation portion of the chip. The fractionation step causes the template nucleic acid fraction to contain the nucleic acid amplification reagent in the template nucleic acid fraction formation portion of the chip.

In the method for analyzing a template nucleic acid of the present invention, for example, the detection step is a step of obtaining an image of the plurality of template nucleic acid fractions on at least one chip and the discrimination step is a step of discriminating the template nucleic acid fraction on the chip in which the generation or quenching of a signal has been detected in the image as the amplified fraction.

In the method for analyzing a template nucleic acid of the present invention, for example, the fractionation step is a step of fractionating the sample into the plurality of template nucleic acid fractions by dropping the sample.

In the fractionation step of the method for analyzing a template nucleic acid of the present invention, for example, an average volume of the plurality of template nucleic acid fractions is 0.0001 to 5000 nL.

In the method for analyzing a template nucleic acid of the present invention, for example, the sample contains at least two template nucleic acids, the nucleic acid amplification reagent contains at least two primer sets and at least two signal generating substances, the at least two primer sets each amplify the target sequence and the complementary sequence in each of different template nucleic acids, and the at least two signal generating substances each have the same fluorescence property and generate or quench a signal in response to an amplification of the target sequence and the complementary sequence in each of the different template nucleic acids.

In the method for analyzing a template nucleic acid of the present invention, for example, the sample contains at least two template nucleic acids, the nucleic acid amplification reagent contains at least two primer sets and at least two signal generating substances, the at least two primer sets each amplify the target sequence and the complementary sequence in each of different template nucleic acids, and the at least two signal generating substances each have a fluorescence property different from each other and generate or quench a signal in response to an amplification of the target sequence and the complementary sequence in each of the different template nucleic acids.

In the method for analyzing a template nucleic acid of the present invention, for example, the sample contains at least two template nucleic acids, the nucleic acid amplification reagent contains at least two primer sets and a non-fluorogenic probe, the at least two primer sets each amplify the target sequence and the complementary sequence in each of different template nucleic acids, and each of the signal generating substance and the non-fluorogenic probe generates or quenches a signal in response to an amplification of the target sequence and the complementary sequence in each of the different template nucleic acids.

In the method for analyzing a template nucleic acid of the present invention, for example, the generation or quenching of a signal that shows an amplification of the target sequence or the complementary sequence is detected with respect to each of the plurality of template nucleic acid fractions before the amplification step. In the discrimination step, by comparing a signal detected before the amplification step and a signal detected after the amplification step, a template nucleic acid fraction in which the generation or quenching of a signal that shows the amplification has been detected among the plurality of template nucleic acid fractions is discriminated as an amplified fraction in which the target sequence or the complementary sequence has been amplified.

In the method for analyzing a template nucleic acid of the present invention, for example, generation or quenching of a signal that shows an amplification of the target sequence or the complementary sequence is detected with respect to the sample containing the template nucleic acid before the fractionation step. In the discrimination step, by comparing a signal detected before the fractionation step and a signal detected after the amplification step, a template nucleic acid fraction in which the generation or quenching of a signal that shows the amplification has been detected among the plurality of template nucleic acid fractions is discriminated as an amplified fraction in which the target sequence or the complementary sequence has been amplified.

In the method for analyzing a template nucleic acid of the present invention, for example, an analysis of the template nucleic acid is an analysis of a modification of the template nucleic acid. The method for analyzing a template nucleic acid of the present invention further includes the step of pretreating the template nucleic acid prior to the amplification step.

In the method for analyzing a template nucleic acid of the present invention, for example, an analysis of the template nucleic acid is an analysis of methylation of the template nucleic acid, and the pretreatment step is a step of converting a non-methylated cytosine residue of the template nucleic acid into a uracil residue or a uracil derivative residue.

In the pretreatment step of the method for analyzing a template nucleic acid of the present invention, for example, the conversion is conducted using bisulfite.

In the method for analyzing a template nucleic acid of the present invention, for example, an analysis of the template nucleic acid is an analysis of methylation of the template nucleic acid, and the pretreatment step is a step of cleaving a non-methylated region or a methylated region of the template nucleic acid.

In the pretreatment step of the method for analyzing a template nucleic acid of the present invention, for example, the cleavage is conducted using a restriction enzyme.

In the method for analyzing a template nucleic acid of the present invention, for example, an analysis of the template nucleic acid is an analysis of methylation of the template nucleic acid, and the pretreatment step is a step of enriching a methylated template nucleic acid.

In the pretreatment step of the method for analyzing a template nucleic acid of the present invention, for example, using at least one of a methylated DNA-binding protein and an anti-methylcytosine antibody, the methylated template nucleic acid is enriched by binding at least one of the methylated DNA-binding protein and the anti-methylcytosine antibody to the methylated template nucleic acid.

In the method for analyzing a template nucleic acid of the present invention, for example, an analysis of the template nucleic acid is an analysis of hydroxymethylation of the template nucleic acid, and the pretreatment step is a step of converting a hydroxymethyl cytosine residue of the template nucleic acid into a non-hydroxymethylated base residue.

In the pretreatment step of the method for analyzing a template nucleic acid of the present invention, for example, a hydroxymethyl cytosine residue is converted into a thymine residue or a thymine derivative residue using a tungsten oxidizing agent.

In the pretreatment step of the method for analyzing a template nucleic acid of the present invention, for example, a hydroxymethyl cytosine residue is converted into a uracil residue or a uracil derivative residue using potassium perruthenate ($KRuO_4$) and bisulfite.

In the method for analyzing a template nucleic acid of the present invention, for example, an analysis of the template nucleic acid is an analysis of hydroxymethylation of the template nucleic acid. The pretreatment step includes the steps of glycosylating a hydroxymethylated region of a hydroxymethylated template nucleic acid; and cleaving the glycosylated region of the hydroxymethylated template nucleic acid.

In the pretreatment step of the method for analyzing a template nucleic acid of the present invention, for example, the cleavage is conducted using a glycosylation-sensitive restriction enzyme.

In the method for analyzing a template nucleic acid of the present invention, for example, an analysis of the template nucleic acid is an analysis of hydroxymethylation of the template nucleic acid. The pretreatment step includes the steps of glycosylating a hydroxymethylated region of a hydroxymethylated template nucleic acid; and enriching the glycosylated hydroxymethylated template nucleic acid.

In the pretreatment step of the method for analyzing a template nucleic acid of the present invention, for example, using a glycosylation hydroxymethylated antibody, the glycosylated hydroxymethylated template nucleic acid is enriched by binding the antibody to the glycosylated hydroxymethylated template nucleic acid.

In the method for analyzing a target substance of the present invention, for example, the target substance is a nucleic acid or a nucleic acid sequence.

In the method for analyzing a target substance of the present invention, for example, the fluorogenic probe is a probe that includes a signal generating substance, and is a probe that generates the signal in a state where it is bound to a target and quenches the signal in a state where it is dissociated from the target or a probe that quenches the signal in a state where it is bound to a target and generates the signal in a state where it is dissociated from the target.

In the method for analyzing a target substance of the present invention, for example, the signal generating substance is fluorogenic.

In the method for analyzing a target substance of the present invention, for example, the fluorogenic probe includes at least two fluorescent atomic groups that exhibit an exciton effect as the signal generating substance per molecule.

In the method for analyzing a target substance of the present invention, for example, a base that includes a pair of fluorescent atomic groups that exhibit an exciton effect has a structure represented by the following formula (16), (16b), (17), or (17b).

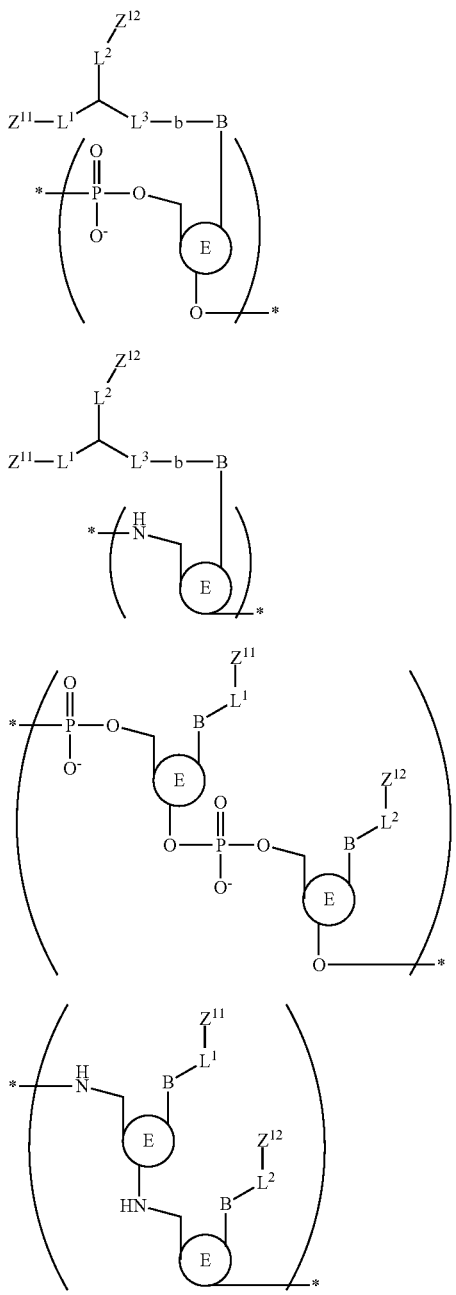

In the method for analyzing a target substance of the present invention, for example, the detection step is a step of detecting brightness or intensity of at least one kind of the signal in the reaction solution.

In the method for analyzing a target substance of the present invention, for example, the detection step is a step of detecting at least one kind of the signal in the reaction solution by counting on the molecular level of the fluorogenic probe.

In the method for analyzing a target substance of the present invention, for example, at least two target substances are analyzed and at least two kinds of target substances are adjacent to each other, at least two fluorogenic probes for the target substances are used, and the fluorogenic probes each include a signal generating substance having a fluorescence property different from each other and generate or quench a signal in response to binding to different target substances with a fluorescence resonance energy transfer.

In the method for analyzing a target substance of the present invention, for example, at least two target substances are analyzed and at least two types of target substances are adjacent to each other, at least two fluorogenic probes for the target substances are used, and the fluorogenic probes each include a signal generating substance having a fluorescence property different from each other, generate or quench a signal in response to binding to different target substances, and detect the presence or absence of a spatial overlap of a plurality of kinds of the signals.

In the contact step and the detection step of the method for analyzing a target substance of the present invention, for example, a temperature of the reaction solution is controlled.

In the method for analyzing a target substance of the present invention, for example, the target substance is a target substance in a state where it is bound to a substance that specifically binds to the target substance. The binding between the target substance and a substance that specifically binds to the target substance may be binding based on the specificity of the target substance of the binding substance or binding not based on the specificity of the target substance of the binding substance, for example. In the latter case, the binding substance can be, for example, a binding substance labeled with the target substance.

In the method for analyzing a target substance of the present invention, for example, an analysis of the target substance is an analysis of a modification of the target substance. The method for analyzing a target substance of the present invention further includes the step of pretreating the target substance prior to the detection step.

The method for analyzing a target substance of the present invention further includes the step of amplifying a pretreated target substance after the pretreatment step and before the detection step, for example. The amplified product obtained in the amplification step is used as the target substance in the detection step.

In the method for analyzing a target substance of the present invention, for example, an analysis of the target substance is an analysis of methylation of the target substance, and the pretreatment step is a step of converting a non-methylated cytosine residue of the target substance into a uracil residue or a uracil derivative residue.

In the pretreatment step of the method for analyzing a target substance of the present invention, for example, the conversion is conducted using bisulfite.

In the method for analyzing a target substance of the present invention, for example, an analysis of the target substance is an analysis of methylation of the target substance, and the pretreatment step is a step of cleaving a non-methylated region or a methylated region of the target substance.

In the pretreatment step of the method for analyzing a target substance of the present invention, for example, the cleavage is conducted using a restriction enzyme.

In the method for analyzing a target substance of the present invention, for example, an analysis of the target substance is an analysis of methylation of the target substance, and the pretreatment step is a step of enriching a methylated target substance.

In the pretreatment step of the method for analyzing a target substance of the present invention, for example, using at least one of a methylated DNA-binding protein and an anti-methylcytosine antibody, the methylated target substance is enriched by binding at least one of the methylated DNA-binding protein and the anti-methylcytosine antibody to the methylated target substance.

In the method for analyzing a target substance of the present invention, for example, an analysis of the target substance is an analysis of hydroxymethylation of the target substance, and the pretreatment step is a step of converting a hydroxymethyl cytosine residue of the target substance into a non-hydroxymethylated base residue.

In the pretreatment step of the method for analyzing a target substance of the present invention, for example, a hydroxymethyl cytosine residue is converted into a thymine residue or a thymine derivative residue using a tungsten oxidizing agent.

In the pretreatment step of the method for analyzing a target substance of the present invention, for example, a hydroxymethyl cytosine residue is converted into a uracil residue or a uracil derivative residue using potassium perruthenate ($KRuO_4$) and bisulfite.

In the method for analyzing a target substance of the present invention, for example, an analysis of the target substance is an analysis of hydroxymethylation of the target substance. The pretreatment step includes the steps of glycosylating a hydroxymethylated region of a hydroxymethylated target substance; and cleaving the glycosylated region of the hydroxymethylated target substance.

In the pretreatment step of the method for analyzing a target substance of the present invention, for example, the cleavage is conducted using a glycosylation-sensitive restriction enzyme.

In the method for analyzing a target substance of the present invention, for example, an analysis of the target substance is an analysis of hydroxymethylation of the target substance. The pretreatment step includes the steps of glycosylating a hydroxymethylated region of a hydroxymethylated target substance; and enriching the glycosylated hydroxymethylated target substance.

In the pretreatment step of the method for analyzing a target substance of the present invention, for example, using a glycosylation hydroxymethylated antibody, the glycosylated hydroxymethylated target substance is enriched by binding the antibody to the glycosylated hydroxymethylated target substance.

In the present invention, the "fractionation" means fractionation conducted by dividing a sample containing the template nucleic acid (hereinafter, also referred to as a "sample") into a plurality of fractions. In the present invention, the "fluorogenic" means, for example, generating a signal in a state of specifically binding to a target substance and quenching a signal in a state of not binding or quenching a signal in a state of specifically binding to a target substance and generating a signal in a state of not binding. The generation and quenching of a signal are reversible. As to the target substance, details are described below. In the case where the target substance is a nucleic acid, the "fluorogenic" means, for example, generating a signal in a state of sequence-dependently binding to a nucleic acid and quenching a signal in a state of not binding or quenching a signal in a state of sequence-dependently binding to a nucleic acid and generating a signal in a state of not binding. The generation and quenching of a signal are reversible. The sequence means, for example, the sequence of a nucleic acid that is the target substance.

In the present invention, the probe can be any substance as long as it specifically binds to the target substance, and examples of the probe include nucleic acids, antibodies, affibodies, and aptamers. In the case where the target substance is a nucleic acid, the probe can be, for example, a nucleic acid probe, an antibody, an affibody, an aptamer, or the like which is complementary to the sequence of the target substance.

The present invention is described below with reference to specific examples. The present invention, however, is not limited by the following description. In the analysis method described below, examples of each step can be combined with examples of other steps, for example, unless otherwise stated.

<Method for Analyzing Template Nucleic Acid>

The method for analyzing a template nucleic acid of the present invention, as described above, includes the steps of fractionating a sample containing a template nucleic acid into a plurality of template nucleic acid fractions; amplifying a target sequence and its complementary sequence in the template nucleic acid with respect to each of the plurality of template nucleic acid fractions in the presence of a nucleic acid amplification reagent; detecting generation or quenching of a signal that shows an amplification of the target sequence or the complementary sequence with respect to each of the plurality of template nucleic acid fractions after the amplification step; and discriminating a template nucleic acid fraction in which the generation or quenching of a signal that shows the amplification has been detected among the plurality of template nucleic acid fractions as an amplified fraction in which the target sequence or the complementary sequence has been amplified, wherein the nucleic acid amplification reagent contains a primer set that amplifies the target sequence and the complementary sequence and a signal generating substance that generates or quenches a signal in response to the amplification, and the signal generating substance generates a signal in a state where it is bound sequence-dependently and quenches a signal in a state where it is not bound or quenches a signal in a state where it is bound sequence-dependently and generates a signal in a state where it is not bound, and generation and quenching of a signal are reversible.

The analysis method of the present invention is characterized in that the sample containing the template nucleic acid is fractionated into the plurality of template nucleic acid fractions in the fractionation step and the generation or quenching of a signal that shows an amplification of the target sequence or the complementary sequence is detected with respect to each of the plurality of template nucleic acid fractions in the detection step after the amplification step, and other steps and conditions are not particularly limited. In the analysis method of the present invention, by fractionating the sample containing the template nucleic acid into a plurality of template nucleic acid fractions, for example, the target sequence and the complementary sequence are amplified after fractionating a plurality of template nucleic acids in the sample into separate template nucleic acid fractions. Furthermore, the amplification is detected using the signal generating substance which is fluorogenic with respect to each template nucleic acid fraction. Thus, according to the analysis method of the present invention, for example, even when the concentration of a template nucleic acid contained in the sample is low to a degree that cannot be detected by a normal gene analysis method, by fractionating the sample in to a plurality of fractions, the template nucleic acid can be enriched in the template nucleic acid fraction including the template nucleic acid. Therefore, according to the analysis method of the present invention, the template nucleic acid can be analyzed accurately. Furthermore, since the analysis method of the present invention using the fluorogenic signal generating substance can detect the template nucleic acid with high specificity, the template nucleic acid can be analyzed more accurately.

The present invention can be applied to any analysis of a template nucleic acid as long as it utilizes the detection of the amplification of the target sequence or the complementary sequence, and contents of the analysis of a template nucleic acid are not particularly limited. The detection of the amplification may be the detection of the amplified product or the detection of association of the amplified product and the probe or dissociation of the associate, for example.

In the present invention, as to "generating a signal in a state of sequence-dependently binding to a nucleic acid and quenching a signal in a state of not binding" or "quenching a signal in a state of sequence-dependently binding to a nucleic acid and generating a signal in a state of not binding", the binding can be, for example, direct sequence-dependent or indirect sequence-dependent. The former case can be, for example, quenching or generation of a signal of a signal generating substance in response to the sequence-dependent binding of the signal generating substance itself of the fluorogenic probe or the fluorogenic primer described below. The latter case can be, for example, quenching or generation of a signal of an intercalator in response to the sequence-dependent binding of a non-fluorogenic probe or a non-fluorogenic primer.

The first example of the analysis of a template nucleic acid in the present invention can be the analysis of the presence or absence of a template nucleic acid (qualitative analysis) or the analysis of the quantity (quantitative analysis). In this case, the target sequence and its complementary sequence in the template nucleic acid are amplified, by detecting the obtained amplified product, the association of the obtained amplified product and the probe, or the dissociation of the associate, the presence or absence or the quantity of the template nucleic acid can be analyzed.

The second example of the analysis of a template nucleic acid in the present invention can be the analysis of a nucleic acid mutation present in a nucleic acid mutation site in the template nucleic acid, which is a so called typing. The nucleic acid mutation site can be, for example, a polymorphism site such as single nucleotide polymorphism. Specific examples of the analysis of the nucleic acid mutation include the discrimination between the wild type and the mutant type at the nucleic acid mutation site, the discrimination between different mutant types at the nucleic acid mutation site, and the discrimination between the homozygote and the heterozygote. In this case, the target sequence and its complementary sequence in the template nucleic acid are amplified, the association of the obtained amplified product and the probe or the dissociation of the associate is detected, and the typing of the nucleic acid mutation site can be conducted from the conditions (e.g., temperature, pH, denaturant concentration, salt concentration, etc.) with which the association or the dissociation occurs.

In the analysis method of the present invention, the target sequence is the sequence of a region containing an arbitrary site in the template sequence, and the complementary sequence is a sequence complementary to the target sequence. In the analysis method of the present invention, the target sequence and the complementary sequence are amplified in the amplification step. There is no particular limitation on the arbitrary site.

When the present invention is applied to typing, the arbitrary site is, for example, a nucleic acid mutation site. The nucleic acid mutation site is, for example, a site in which an intended nucleic acid mutation to be detected is present in the template nucleic acid. In this case, the target sequence is the sequence of a region containing the nucleic acid mutation site in the template nucleic acid, and the complementary sequence is a sequence complementary to the target sequence.

In the analysis method of the present invention, the sample is not particularly limited and samples having the possibility of including a template nucleic acid or the target substance described below can be used. Examples of the target substance include various nucleic acids such as DNAs and RNAs. Examples of the sample include organism-origin samples, food and beverage-origin samples, and environment-origin samples. The organism is not particularly limited, and examples thereof include animals including humans; nonhuman mammals such as cattle, pigs, sheep, mice, rats, rabbits, and horses; birds; and fish. Examples of the organism-origin sample include body fluids, tissues, and cells in organisms. Examples of the body fluid include blood such as whole blood, blood cell, blood plasma, blood serum, and the like; intraocular fluids such as aqueous humor and the like; lymph; cerebrospinal fluids; tears; sweat; semen; saliva; mucus; urine; nasal discharge; and nasal swab. Examples of the tissue include intraocular tissues such as vitreous body and the like; and tissues having a pathogen such as a tumor and the like. Examples of the food and beverage-origin sample include beverages, food, and food raw materials. The present invention can be, for example, applied to infection inspection, food poisoning inspection, and the like. Examples of the environment-origin sample include water; seawater; fresh water; river water; lake water; groundwater; wastewater; sewage; soil; atmosphere; and adhered matters in food-processing factories, kitchens, and the like. The sample contains, for example, a template nucleic acid, the target substance described above, and the like. The origin of the sample is not particularly limited and can be, for example, humans, nonhuman animals, and the like.

In the analysis method of the present invention, the template nucleic acid can be, for example, a nucleic acid sample or the like. The nucleic acid sample can be, for example, a single-stranded nucleic acid or a double-stranded nucleic acid. In the former case, for example, the single-stranded nucleic acid is the template nucleic acid. In the latter case, for example, either one of a pair of single-stranded nucleic acids that compose the double-stranded nucleic acid may be set as a template nucleic acid including the target sequence. Specifically, for example, a sense strand of the pair of single-stranded nucleic acids may be set as a template nucleic acid including the target sequence or an antisense strand of the pair of single-stranded nucleic acids may be set as a template nucleic acid including the target sequence.

Examples of the template nucleic acid include nucleic acids such as DNAs and RNAs. The nucleic acid is, for example, a nucleic acid originated from the sample. The sample-origin DNA may be, for example, DNA contained in the sample or cDNA generated from RNA contained in the sample by reverse transcription. Examples of RNA contained in the sample include total RNAs and mRNAs. The nucleic acid may be, for example, circulating tumor DNAs (ctDNAs) and circulating tumor RNAs (ctRNAs).

In the analysis method of the present invention, the template nucleic acid may be, for example, a template nucleic acid complex containing substances other than the nucleic acid. Specifically, the template nucleic acid complex may further contain a target substance and a binding substance that specifically binds to the target substance, for example. In this case, the binding substance is directly bound to the template nucleic acid, for example, and it can be said as a binding substance labeled with the template nucleic acid. The direct bond is, for example, covalent bond. The target substance is not particularly limited, and reference can be made to the description below, for example. The binding substance can be any substance as long as it can specifically bind to the target substance, for example. Specifically, reference can be made to the description as to the probe. The template nucleic acid complex can be formed by bringing a sample containing the target substance into contact with a binding substance labeled with the template nucleic acid, for example. In the case where the template nucleic acid is the complex of the template nucleic acids, preferably, the template nucleic acid is DNA having a sequence which is artificially designed, for example.

In the present invention, the number of kinds of a template nucleic acid contained in the sample is at least 1, and is, for example, at least 2, at least 5, or at least 20. The upper limit of the number of kinds of a template nucleic acid is not particularly limited and is, for example, at most 200, at most 100, and at most 50, and the range is, for example, 1 to 200, 2 to 100, or 5 to 50.

In the analysis method of the present invention, the nucleic acid amplification reagent can be discriminated based on the amplification method adopted in the amplification step described below, for example. Specifically, the nucleic acid amplification reagent contains a primer set that amplifies the target sequence and the complementary sequence and a signal generating substance that generates or quenches a signal in response to the amplification. The kind of the primer set is not particularly limited, and reference can be made to the examples of the kind of the template nucleic acid, for example. The number of kinds of the primer set may be, for example, the same number as or a different number from the number of kinds of the template nucleic acid. When the sample contains at least two template nucleic acids, the primer set may be designed such that one primer set can amplify at least two template nucleic acids, for example. When the nucleic acid amplification reagent contains at least two primer sets, the primer sets each may amplify the target sequence and the complementary sequence in the same template nucleic acid or may amplify the target sequence and the complementary sequence in different template nucleic acids, and the latter is preferable.

The primer set is described in detail. Hereinafter, in the primer set, a primer that synthesizes the target sequence is also referred to as a "first primer" and a primer that synthesizes the complementary sequence is also referred to as a "second primer".

In the analysis method of the present invention, the polymerase primed from the 3' end of the first primer synthesizes the target sequence and the polymerase primed from the 3' end of the second primer synthesizes the complementary sequence. The first primer and the second primer can be determined appropriately according to the sequence of the template nucleic acid, for example.

Regarding the first primer and the second primer, for example, reference can be made to FIG. 1. FIG. 1 is a schematic view showing the relationship between the template nucleic acid and the first primer and the relationship between the template nucleic acid and the second primer. In FIG. 1, an outline region denotes a region having the same sequence as a corresponding site of the template nucleic acid, and a solid region denotes a region having a sequence complementary to a corresponding site of the template nucleic acid (hereinafter, the same applies). As shown in FIG. 1, the first primer has the same sequence as an upstream region of an arbitrary site (e.g., the nucleic acid mutation site) in the template nucleic acid, for example. The first primer may only contain the same sequence or may contain the same sequence and other sequence(s), for example. In the latter case, preferably, the first primer has the same sequence at its 3' end region. The second primer has a sequence complementary to a downstream region of an arbitrary site (e.g., the nucleic acid mutation site) in the template nucleic acid, for example. The second primer may only contain the complementary sequence or may contain the complementary sequence and other sequence(s), for example. In the latter case, preferably, the second primer has the complementary sequence at its 3' end region. When the nucleic acid amplification reagent contains at least two primer sets, the first primers of the at least two primer sets may be sequences complementary to the same sequence or sequences complementary to different sequences, and the latter is preferable. Also, the second primers of the at least two primer sets may be sequences complementary to the same sequence or sequences complementary to different sequences, and the latter is preferable.

In the analysis method of the present invention, the signal generating substance can be any substance as long as it is fluorogenic. The signal generating substance is preferably added to a binding substance that specifically binds to the target sequence or the complementary sequence, for example. That is, the signal generating substance is preferably used as a signal generating binding substance including the signal generating substance or a primer including the signal generating substance. When the nucleic acid amplification reagent contains at least two signal generating substances, the signal generating substances may be signal generating substances of the same kind or may be signal generating substances of different kinds. The kind of the signal generating substance is not particularly limited, and reference can be made to the examples of the kind of the template nucleic acid, for example. The number of kinds of the signal generating substance may be, for example, the same number as or a different number from the number of kinds of the template nucleic acid and/or the primer set. When the sample contains at least two template nucleic acids, one signal generating substance may generate or quench a signal in response to the amplification of the target sequences and the complementary sequences in at least two template nucleic acids, for example. When the nucleic acid amplification reagent contains at least two signal generating substances, the signal generating substances may each have the same fluorescence property or a fluorescence property different from each other, for example, and the latter is preferable as it allows at least two template nucleic acids to be analyzed simply. Examples of the fluorescence property include an excitation wavelength and a fluorescence wavelength. Having the same fluorescence property means, for example, having the same excitation wavelength and the same fluorescence wavelength. Having a different fluorescence property means, for example, having a different excitation wavelength or a different fluorescence wavelength. When the nucleic acid amplification reagent contains at least two signal generating substances, preferably, the signal generating substances each generate or quench a signal in response to the amplification of each of the target sequences and the complementary sequences in different template nucleic acids as it allows at least two template nucleic acids to be analyzed simply. When the nucleic acid amplification reagent contains at least two signal generating substances, as to the generation or quenching of a signal, for example, a fluorescence resonance energy transfer (FRET) may be utilized or may not be utilized.

The signal generating binding substance including the signal generating substance can be, for example, a substance that specifically binds to the target sequence or the complementary sequence. The signal generating binding substance including the signal generating substance may be, for example, a substance that generates the signal in a state where it is bound to a target and quenches the signal in a state where it is dissociated from the target or a substance that quenches the signal in a state where it is bound to a target and generates the signal in a state where it is dissociated from the target. Specifically, the signal generating binding substance including the signal generating substance can be, for example, a fluorogenic probe including the signal generating substance. In this case, the fluorogenic probe may be, for example, a probe that generates the signal in a state where it is bound to a target and quenches the signal in a state where it is dissociated from the target or a probe that quenches the signal in a state where it is bound to a target and generates the signal in a state where it is dissociated from the target.

The signal generating substance of the fluorogenic probe can be, as described above, any substance as long as it is fluorogenic. Specific examples of the signal generating substance include a substance that exhibits a fluorescence quenching phenomenon and a fluorescent atomic group that exhibits an exciton effect. Specific examples of the fluorogenic probe include a probe including a substance that exhibits a fluorescence quenching phenomenon (Quenching phenomenon probe (hereinafter, also referred to as a "Q probe")), a probe including at least two fluorescent atomic groups that exhibit an exciton effect as the signal generating substance per molecule (hereinafter, also referred to as an "E probe"), and a molecular beacon. When the nucleic acid amplification reagent contains at least two fluorogenic probes, the fluorogenic probes may be fluorogenic probes of the same kind or may be fluorogenic probes of different kinds.

The fluorogenic probe may be a probe that hybridizes to the target sequence including the arbitrary site or a probe that hybridizes to the complementary sequence. The probe can be determined appropriately according to the sequence of the template nucleic acid, for example. When the nucleic acid amplification reagent contains at least two fluorogenic probes, the fluorogenic probes may be probes that hybridize to the same sequence or probes that hybridize to different sequences, and the latter is preferable. The former probe has a sequence that hybridizes to the target sequence, for example. The probe may only contain the sequence that hybridizes to the target sequence or may contain the sequence that hybridizes to the target sequence and other sequence(s). The latter probe has a sequence that hybridizes to the complementary sequence, for example. The probe may only contain the sequence that hybridizes to the complementary sequence or may contain the sequence that hybridizes to the complementary sequence and other sequence(s).

Regarding the probe, reference can be made to FIG. 1, for example. FIG. 1 is a schematic view showing the relationship between the template nucleic acid and the probes. As shown in FIG. 1, when the probe is a probe that hybridizes to the target sequence (Tseq probe), for example, the probe may be designed to contain a sequence complementary to a region containing an arbitrary site N (e.g., the nucleic acid mutation site) in the template nucleic acid. In the Tseq probe, a site corresponding to an arbitrary site N in the template nucleic acid includes Nc complementary to the arbitrary site N. When the probe is a probe that hybridizes to the complementary sequence (Cseq probe), for example, the probe may be designed to contain the same sequence as a region containing an arbitrary site (e.g., the nucleic acid mutation site) in the template nucleic acid.

When the analysis method of the present invention is applied to typing, the base of the nucleic acid mutation site in the template nucleic acid may be a wild type or a mutant type, for example. When there is a plurality of mutant types, the base may be any of the mutant types.

When the analysis method of the present invention is applied to typing, it can be said that the probe is, for example, a typing probe. As to the probe, for example, there are the following first embodiment and second embodiment. In the first embodiment, the dissociation temperature or the association temperature differs between the case where the probe mismatches with the nucleic acid mutation site and the case where the probe fully matches with the nucleic acid mutation site, and the probe can detect the nucleic acid mutation of the nucleic acid mutation site based on the dissociation temperature or the association temperature. The probe of the first embodiment can determine whether the probe mismatches with the nucleic acid mutation site or fully matches with the nucleic acid mutation site based on the dissociation temperature or the association temperature. As a result, the probe of the first embodiment can detect whether the base of the nucleic acid mutation site is an intended mutation (e.g., mutant type or wild type). When the probe is, for example, a probe mt that fully matches with a mutant type nucleic acid mutation site, the probe mt shows a stronger association power to a mutant type target sequence mt having the nucleic acid mutation site with which the probe fully matches than a wild type target sequence wt having the nucleic acid mutation site with which the probe mismatches. Thus, the association temperature of the probe mt and the mutant type target sequence mt is higher than the association temperature of the probe mt and the wild type target sequence wt.

In the second embodiment, the dissociation temperature or the association temperature differs between the case where the probe mismatches with the nucleic acid mutation site and the case where the probe mismatches with the nucleic acid mutation site with a different melting temperature (Tm) value, and the probe can detect the nucleic acid mutation of the nucleic acid mutation site based on the dissociation temperature or the association temperature. The probe of the second embodiment can determine which one of the mismatches is present based on the dissociation temperature or the association temperature. As a result, the probe of the second embodiment can detect whether the base of the nucleic acid mutation site is an intended mutation (e.g., mutant type or wild type).

The E probe is, as described above, a probe including at least two fluorescent atomic groups that exhibit an exciton effect as the signal generating substance per molecule. Regarding the E probe, for example, reference can be made to Japanese Patent No. 4370385 and WO2014/013954.

In the base sequence of the probe that composes the E probe, the binding position where the two fluorescent atomic groups are bound is not limited to particular positions, and can be any position. The binding position can be, for example, the same base or two adjacent bases in the probe. The two fluorescent atomic groups may be directly bound to the probe or indirectly bound to the probe, for example. In the latter case, the two fluorescent atomic groups are bound to the probe through a linker, for example.

The E probe is a probe into which two fluorescent atomic groups (e.g. thiazole orange and its similar substance) are introduced. The E probe has a property of hardly emitting fluorescence due to the exciton effect obtained when two fluorescent atomic groups form exciplex in the case of single strand but strongly emitting fluorescence with the exciton effect being resolved when two fluorescent atomic groups move away from each other upon its hybridization to a target. Note here that while the "E probe" is the trade name of product of Kabushiki Kaisha DNAFORM ("Eprobe" is a registered trademark), the "E probe" in the present invention may be identical to or different from a product given the trade name of the "E probe" or the "Eprobe".

The 3' end of the E probe may be modified such that it cannot be extended, for example. Specifically, for example, the 3' end of the E probe may be chemically modified with a linker OH group.

In the E probe, fluorescent atomic groups that exhibit an exciton effect are each:

(i) the one that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid, (ii) the one composed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to a target molecule, e.g. a nucleic acid, or (iii) the one characterized in having a chemical structure of at least two dye molecules contained in one molecule, with the at least two dye molecules not exhibiting fluorescence emission due to the exciton effect obtained when they aggregate in parallel to each other but exhibiting fluorescence emission with the aggregation state being resolved when the molecules undergo intercalation into or groove binding to a target molecule, e.g. a nucleic acid. In the case of (ii) or (iii), it is preferable that the dye molecule is the molecule described in (i).

In the E probe, the structure of the nucleic acid molecule may be, for example, a labeled nucleic acid containing at least one of the structures represented by the following formulae (16), (16b), (17), (17b), (18), and (18b). In the present invention, the labeled nucleic acid also encompasses tautomers and stereoisomers of these structures, as well as salts of these structures, tautomers, and stereoisomers. Hereinafter, the structures represented by the following respective formulae and having atomic groups $Z^{11}$ and $Z^{12}$ that exhibit fluorescence may each be referred to as a "labeled structure". The labeled nucleic acid containing the labeled structure may be referred to as a "labeled probe".

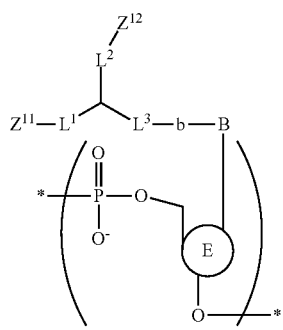

(16)

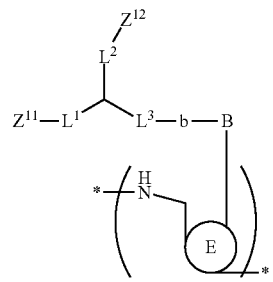

(16b)

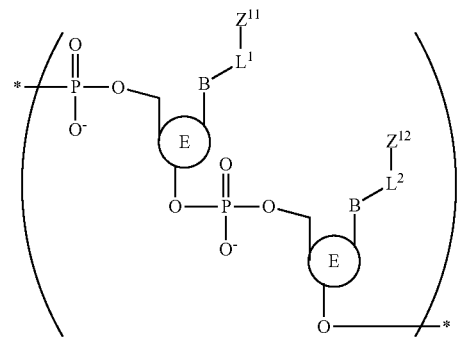

(17)

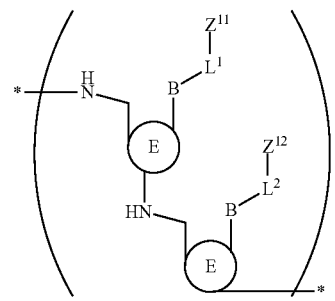

(17b)

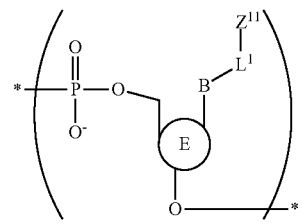

(18)

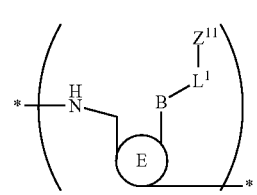

(18b)

In the formulae (16), (16b), (17), (17b), (18), and (18b),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each an atomic group exhibiting fluorescence, and may be identical to or different from each other, L¹, L², and L³ are each a linker (a linking atom or an atomic group), the main chain length (the number of main chain atoms) thereof is arbitrary, L¹, L², and L³ each may or may not contain each of C, N, O, S, P, and Si in the main chain, L¹, L², and L³ each may or may not contain each of a single bond, a double bond, a triple bond, an amide bond, an ester bond, a disulfide bond, an imino group, an ether bond, a thioether bond, and a thioester bond in the main chain, and L¹, L², and L³ may be identical to or different from each other, D is CR, N, P, P=O, B, or SiR where R is a hydrogen atom, an alkyl group, or an arbitrary substituent, and b is a single bond, a double bond, or a triple bond, or alternatively, in the formulae (16) and (16b), L¹ and L² are each a linker, L³, D, and b may not be present, and L¹ and L² may be bonded directly to B, provided that:

in the formulae (16), (17), and (18), E is an atomic group described in the item (i), and at least one O atom in a phosphoric acid linkage may be substituted with an S atom;

in the formulae (16b), (17b), and (18b), E is an atomic group described in the item (ii); and in the formulae (17) and (17b), the respective Bs may be identical to or different from each other, and the respective Es may be identical to or different from each other.

In the formulae (16), (17), (16b), (17b), (18), and (18b), the main chain length (the number of main chain atoms) of each of L¹, L², and L³ preferably is an integer of 2 or more. The upper limit thereof is not particularly limited, and is, for example, 100 or less, more preferably 30 or less, and particularly preferably 10 or less.

$Z^{11}$ and $Z^{12}$ are fluorescent atomic groups that exhibit an exciton effect. This allows the environment around the fluorescent dyes to be changed when the probe is bound to a target sequence, for example, fluorescence to be increased greatly when a double helix structure is formed, so that the target sequence can be detected further effectively.

$Z^{11}$ and $Z^{12}$ are not particularly limited as long as they are fluorescent atomic groups that exhibit an exciton effect. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and a quinoline ring being linked to each other with a methine group. It usually exhibits weak fluorescence but gives strong fluorescence emission by intercalating into DNA having a double helix structure. Other examples include dyes such as fluorescein and Cy3.

More preferably, $Z^{11}$ and $Z^{12}$ are each independently an atomic group represented by any one of the following formulae (7) to (9).

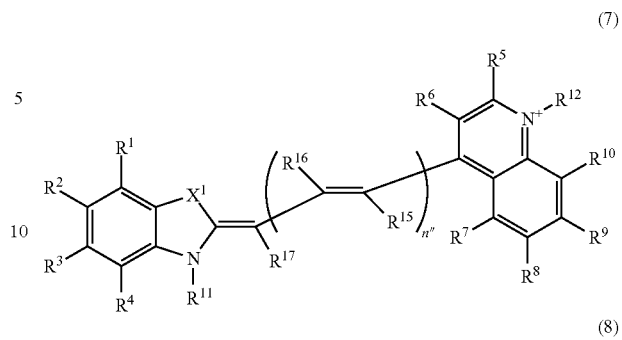

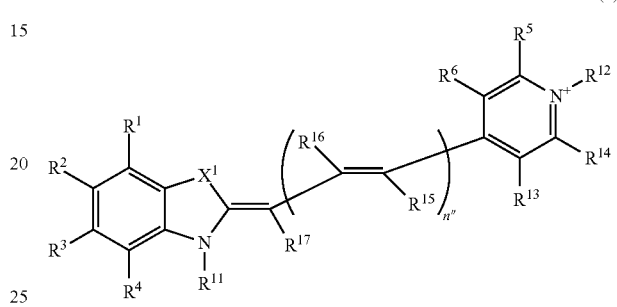

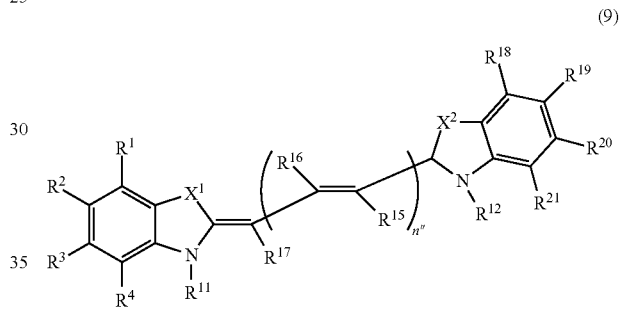

In the formulae (7) to (9), $X^1$ and $X^2$ are S, O, or Se, n" is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that is bound to $L^1$ or $L^2$ in the formulae (16), (17), (16b), (17b), (18), and (18b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

In the formulae (7) to (9), it is more preferable that, in $R^1$ to $R^{21}$, the lower alkyl group is a linear or branched alkyl group with a carbon number of 1 to 6, and the lower alkoxy group is a linear or branched alkoxy group with a carbon number of 1 to 6.

In the formulae (7) to (9), it is more preferable that in $R^{11}$ and $R^{12}$, the linking group is a polymethylene carbonyl group with a carbon number of at least 2 and is bound to $L^1$ or $L^2$ in the formula in the formula (16), (17), (16b), (17b), (18) or (18b) in the carbonyl group moiety. The upper limit of the carbon number of the polymethylene carbonyl group is not particularly limited, and is, for example, 100 or less, preferably 50 or less, more preferably 30 or less, and particularly preferably 10 or less.

When $Z^{11}$ and $Z^{12}$ are each represented by any one of the formulae (7) to (9), it is more preferable that they are, for example, each independently a group represented by formula (19) or (20).

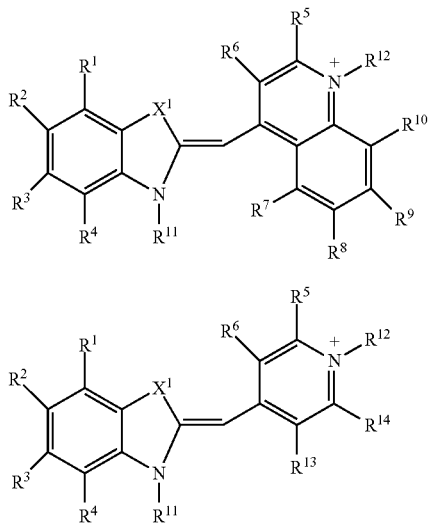

(19)

(20)

In the formulae (19) and (20), $X^1$ denotes —S— or —O—. $R^1$ to $R^{10}$ and $R^{13}$ and $R^{14}$ each independently indicates a hydrogen atom, a halogen atom, a lower alkyl group, a lower alkoxy group, a nitro group, or an amino group. One of $R^{11}$ and $R^{12}$ is a linking group that is bound to $L^1$ or $L^2$ in the formulae (16), (17), (16b), (17b), (18), and (18b), and the other is a hydrogen atom or a lower alkyl group.

Particularly preferably, $Z^{11}$ and $Z^{12}$ are each independently an atomic group represented by any one of the following chemical formulae.

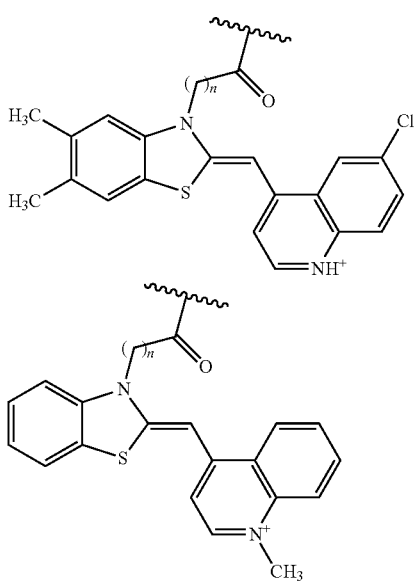

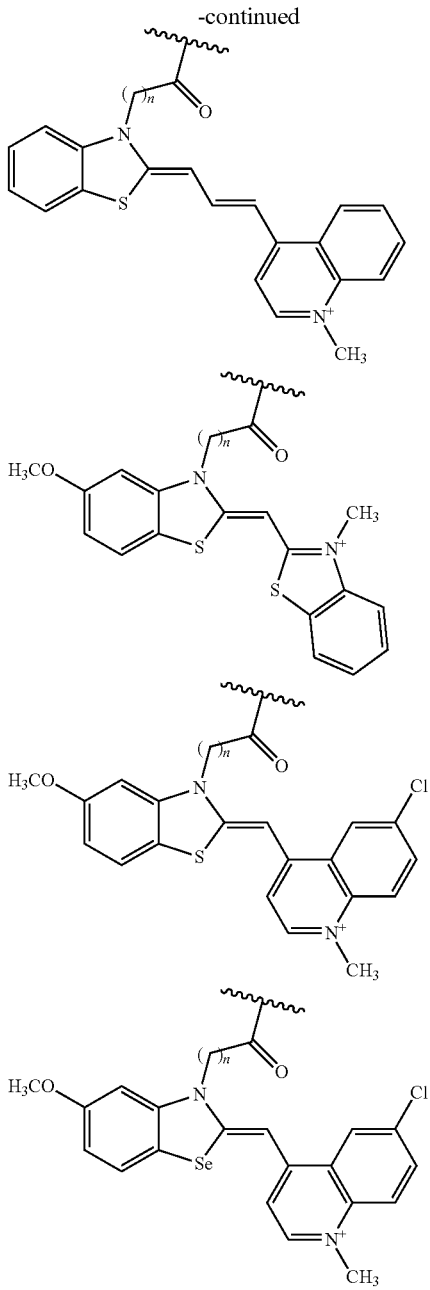

In each of the above chemical formulae, it is particularly preferable that n is a positive integer and in the range from 2 to 6.

In the formulae (16), (17), (16b), (17b), (18), and (18b), B may have a natural nucleobase skeleton, and also, as described above, may have an artificial nucleobase skeleton. For example, B preferably is a structure represented by Py (pyrimidine ring), Py der., Pu (purine ring), or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

(11)

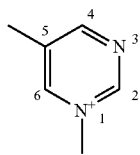

(12)

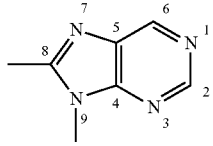

The nucleic acid molecule in the E probe may include, for example, at least one of structures represented by the following chemical formulae 106, 110, 113, 117, 120, 122, 123, 124, and 114-2, geometric isomers and stereoisomers thereof, and salts thereof.

106

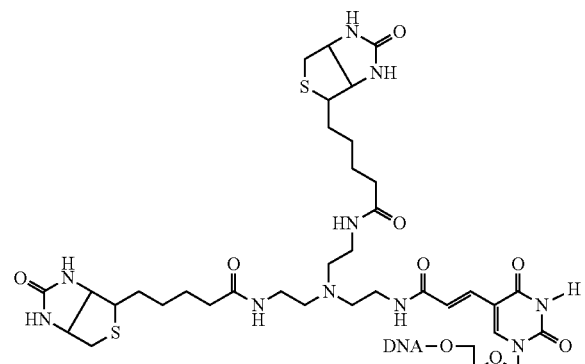
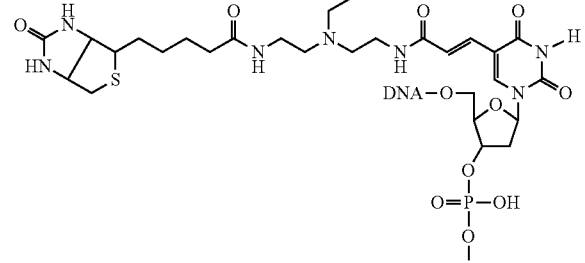

110

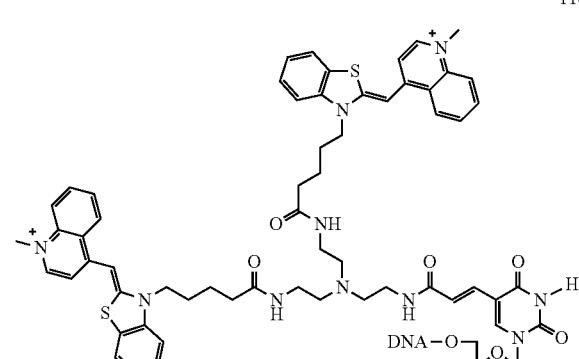

113

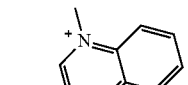
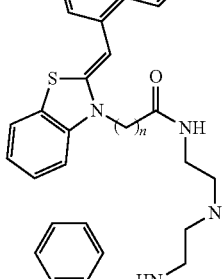
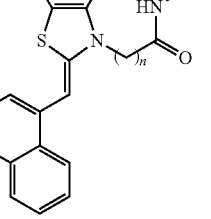
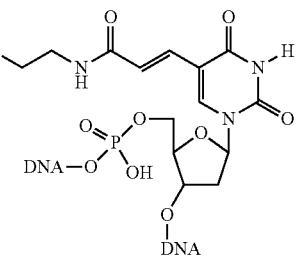

117

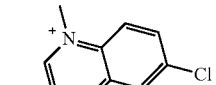
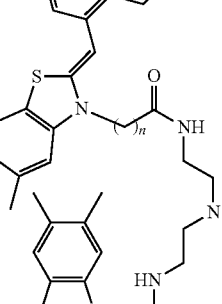
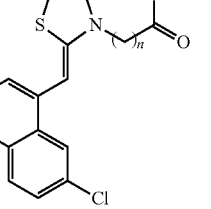
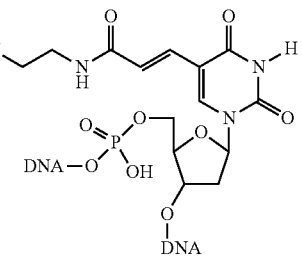

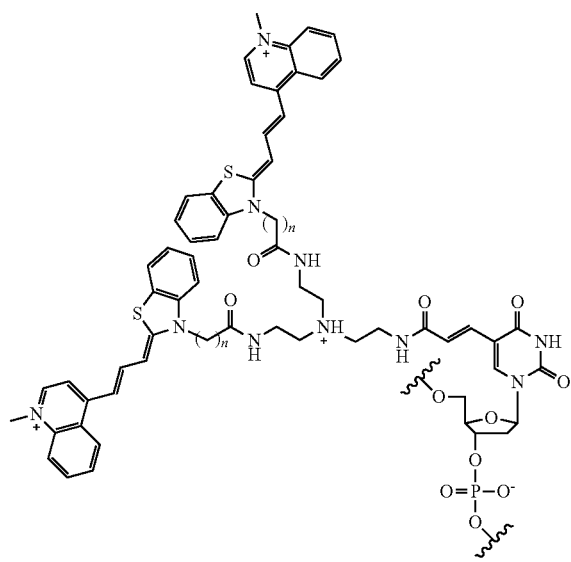
(120)
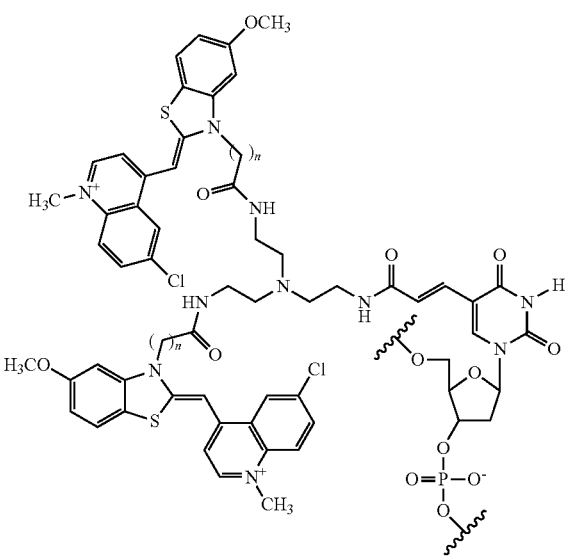
(123)
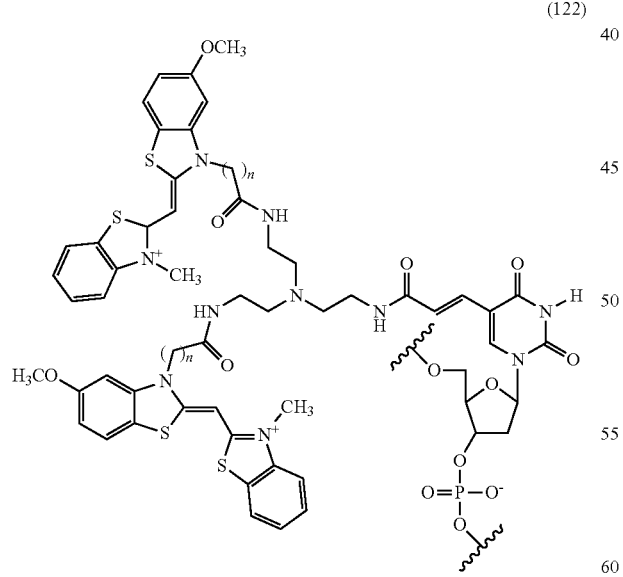
(122)
(124)

-continued (114-2)

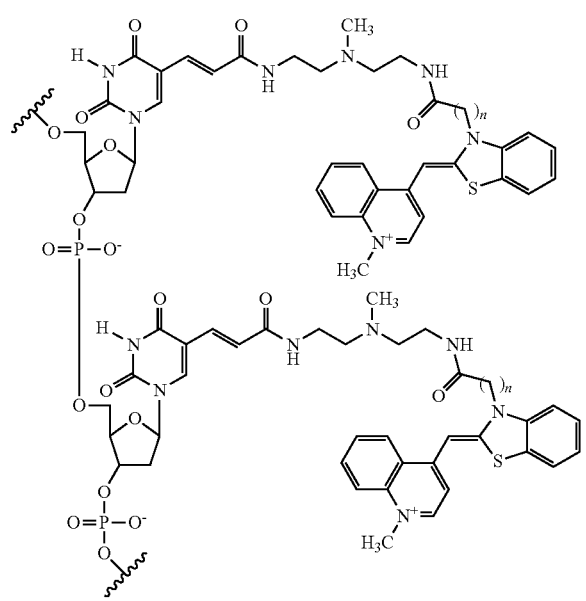

In the chemical formulae 106, 110, 113, 117, 120, 122, 123, 124, and 114-2, the linker length n preferably is a positive integer and in the range from 2 to 6.

The number of the labeled structures contained in the E probe is not particularly limited, and is, for example, about 1 to 100 or about 1 to 20. In the E probe, the site at which the labeled structure is included also is not particularly limited.

The probe may be composed any one of a natural nucleotide residue, a non-nucleotide residue, a modified nucleotide residue, and an unnatural main skeleton, for example, and the probe may contain one of, two of, three of, or four of them. The unnatural main skeleton is not particularly limited, and examples thereof include LNAs, PNAs, and nucleic acids having a modified phosphodiester bond. Furthermore, the modified nucleotide residue is not particularly limited, and can be a phosphorothioate nucleotide residue, and the nucleotide residue may contain a sulfur atom (S) or may be modified with a sulfur atom (S).

The basic skeleton of the probe is not particularly limited. Examples thereof include oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), chimeric molecules thereof, and other structures. Furthermore, the basic skeleton of the nucleic acid may be a natural one or an artificially synthesized one. When the nucleic acid is a probe, the nucleic acid is not particularly limited as long as it can provide base pairing, for example. When the nucleic acid is a nucleic acid sample or a target nucleic acid sequence, the nucleic acid is not particularly limited as long as, for example, it serves as a template for synthesizing a complementary strand. Therefore, the nucleic acid may be a nucleotide derivative, a part or the whole of which is composed of a completely artificial structure, for example. Examples of artificial bases that compose the nucleic acid include, but not limited to, 2-amino-6-(N,N-dimethylamino)purine pyridin-2-one, 5-methylpyridin-2-one, 2-amino-6-(2-thienyl)purine, pyrrole-2-carbaldehyde, 9-methylimidazo[(4,5)-b]pyridine, 5-iodo-2-oxo(1H)pyridine 2-oxo-(1H)pyridine, 2-amino-6-(2-thiazolyl)purine, and 7-(2-thienyl)-imidazo[4,5-b]pyridine.

In the analysis method of the present invention, the "nucleotide" may be either deoxynucleotide or ribonucleotide, for example, and the "oligonucleotide" and "polynucleotide" may each be composed of either one of deoxynucleotide and ribonucleotide or may contain both of them. In the probe, the number of bases that compose the nucleic acid is not particularly limited. Generally, the term "nucleic acid" is synonymous with the term "polynucleotide". Generally, the term "oligonucleotide" is used as a term indicating a polynucleotide composed of a particularly small number of bases, among others. In general, a polynucleotide of, for example, 2- to 100-mer, more generally about 2- to 50-mer is referred to as "oligonucleotide", but it is not limited by these numerical values. In the first analysis method, the term "polynucleotide" also should be interpreted to encompass, for example, polynucleotide and oligonucleotide, as well as artificially synthesized nucleic acids such as peptide nucleic acid, morpholine nucleic acid, methylphosphonate nucleic acid, and S-oligonucleic acid.

Generally, the peptide nucleic acid (PNA) has a structure in which a deoxyribose main chain of oligonucleotide has been substituted with a peptide main chain. Examples of the peptide main chain include a repeating unit of N-(2-aminoethyl)glycine bound by an amide bond. Examples of the base to be bound to the peptide main chain of PNA include, but are not limited to: naturally-occurring bases such as thymine, cytosine, adenine, guanine, inosine, uracil, 5-methylcytosine, thiouracil, and 2,6-diaminopurine; and artificial bases such as bromothymine, azaadenine, and azaguanine.

Generally, LNA is a nucleic acid having two cyclic structures in which, in a sugar-phosphoric acid skeleton, an oxygen atom in the 2'-position and a carbon atom in the 4'-position of ribose are bound to each other by methylene crosslinking. When oligonucleotide containing LNA anneals to DNA, the double-stranded conformation is changed, whereby thermal stability is improved. LNA has a stronger binding affinity to a nucleic acid than common oligonucleotide. Thus, for example, by appropriately setting the conditions of oligonucleotide design, more reliable and stronger hybridization can be achieved.

The number of bases contained in the probe is not particularly limited, and may be, for example, about 5 to about 100, about 6 to 50, or about 6 to 25.

The fluorogenic primer set including a signal generating substance may be, for example, a primer that generates the signal in a state where it is bound to a target and quenches the signal in a state where it is dissociated from the target or a primer that quenches the signal in a state where it is bound to a target and generates the signal in a state where it is dissociated from the target.

The signal generating substance of the fluorogenic primer can be, as described above, any substance as long as it is fluorogenic. Specific examples of the signal generating substance include a substance that exhibits a fluorescence quenching phenomenon and a fluorescent atomic group that exhibits an exciton effect. Specific examples of the fluorogenic primer include a primer including a substance that exhibits a fluorescence quenching phenomenon (Quenching phenomenon primer (hereinafter, also referred to as a "Q primer")) and a primer including at least two fluorescent atomic groups that exhibit an exciton effect as the signal generating substance per molecule (hereinafter, also referred to as an "E primer").

The E primer is, as described above, a primer including at least two fluorescent atomic groups that exhibit an exciton effect as the signal generating substance per molecule. Regarding the E primer, reference can be made to the description as to the E probe by replacing "E probe" with "E primer" and "probe" with "primer", unless otherwise stated. The number of the labeled structures contained in the E primer is not particularly limited, and is, for example, 1 to 100 or 1 to 20. In the E primer, a site containing the labeled structure is not particularly limited.

The number of bases contained in the primer is not particularly limited, and may be, for example, about 5 to about 100, about 6 to 50, or about 6 to 25.

In the analysis method of the present invention, the nucleic acid amplification reagent may contain other reagents, for example. Examples of the other reagent include a non-fluorogenic probe, an enzyme such as polymerase, and monomer nucleic acid (dNTP) for amplification. For example, the sample containing the template nucleic acid may be caused to preliminarily contain the nucleic acid amplification reagent, the sample containing the template nucleic acid may be caused to contain the nucleic acid amplification reagent in the fractionation step, the template nucleic acid fractions may each be caused to contain the nucleic acid amplification reagent in the fractionation step, or the template nucleic acid fractions may each be caused to contain the nucleic acid amplification reagent after the fractionation step and before the amplification step. When the sample containing the template nucleic acid contains the nucleic acid amplification reagent, the sample containing the template nucleic acid and the nucleic acid amplification reagent may be fractionated into the plurality of fractions in the fractionation step described below.

The non-fluorogenic probe is a probe that generates or quenches a signal in response to the amplification of the target sequence and the complementary sequence in the template nucleic acid. The non-fluorogenic probe is a probe which is not fluorogenic, and can be, for example, a probe which is not the fluorogenic probe. Examples of the non-fluorogenic probe include fluorescence-labeled probes labeled with fluorescence substances. Specifically, the examples include a TAQMAN® probe, a cycling probe, an ALEXA FLUOR® probe, and QDOT®. In the analysis method of the present invention, an intercalator such as SYBR® Green can be used in place of the non-fluorogenic probe, for example. Regarding the position and sequence of the non-fluorogenic probe to be hybridized to an intended sequence, for example, reference can be made to the description as to the position and sequence of the fluorogenic probe to be hybridized to an intended sequence. When the nucleic acid amplification reagent contains a non-fluorogenic probe, the kind of the non-fluorogenic probe is not particularly limited, and reference can be made to the examples of the kind of the template nucleic acid, for example. The total number of the kinds of the non-fluorogenic probe and the kinds of the signal generating substance is preferably the same as the number of the kinds of the template nucleic acid, for example. When the nucleic acid amplification reagent contains a non-fluorogenic probe, the signal generating substance and the non-fluorogenic probe may generate or quench signals in response to the amplification of the target sequence and the complementary sequence in the same template nucleic acid or may generate or quench signals in response to the amplification of the target sequences and the complementary sequences in the different template nucleic acids, and the latter is preferable as it allows at least two template nucleic acids to be analyzed simply.

In the fractionation step, the average volume of the plurality of template nucleic acid fraction is not particularly limited and is, for example, 0.0001 to 5000 nL, 0.0001 to 2000 nL, 0.005 to 2000 nL, 0.005 to 1000 nL, 0.01 to 1000 nL, 0.05 to 500 nL, 0.1 to 500 nL, 0.2 to 500 nL, 0.5 to 500 nL, 0.5 to 200 nL, 0.5 to 100 nL, 1 to 100 nL, 1 to 50 nL, 2 to 50 nL, or 5 to 50 nL.

In the analysis method of the present invention, preferably, each step is performed in a reaction solution, for example. The reaction solution may contain a necessary reagent appropriately according to the type of the amplification method, for example.

1. Fractionation Step

In the fractionation step, the sample containing the template nucleic acid is fractionated into the plurality of template nucleic acid fractions. In the fractionation step, the method for fractionating the sample is not particularly limited, and the method can be, for example, a method for fractionating the sample into the plurality of template nucleic acid fractions by dropping the sample. As a specific example, the fractionation step includes, for example, the following step (1-1) or step (1-2).

(1-1) Step of forming an emulsion from the sample (1-2) Step of fractionating the sample into the plurality of template nucleic acid fractions by dispensing the sample to a chip provided with a plurality of fraction formation portions on its surface Step (1-1)

In the step (1-1), an emulsion is formed from the sample. In the emulsion, the template nucleic acid fraction is a drop of the sample dispersed in the emulsion. The emulsion can be formed using a water-insoluble solvent and a water-soluble solvent (aqueous solvent), which form an emulsion, by bringing the water-insoluble solvent into contact with the water-soluble solvent in the presence of the sample to form a plurality of drops in the water-insoluble solvent. Regarding the contact, for example, the water-soluble solvent may be brought into contact with the water-insoluble solvent or the water-insoluble solvent may be brought into contact with the water-soluble solvent. The formation method can be, for example, a droplet formation method using a micro flow channel (e.g., RAINDROP® System produced by Rain-Dance Technologies, QX200® AUTODG® Droplet Digital PCR system produced by BIO-RAD, etc.). The sample may be contained in a water-insoluble solvent or in water-soluble solvent, for example. When the template nucleic acid is, for example, a sample dispersed in the water-soluble solvent, the sample may be used as the water-soluble solvent. As to the emulsion formation, a common method for forming an emulsion can be used. The emulsion formation method is not particularly limited, and an emulsifying device can be used, for example. The emulsifying device can be, for example, a flow channel provided with a sample flow channel, a nucleic acid amplification reagent flow channel, a water-insoluble solvent flow channel, a coupling portion thereof, and a delivery flow channel delivered from the coupling portion. When the emulsifying device is used, for example, the water-insoluble solvent is introduced into the coupling portion from the water-insoluble solvent flow channel, and then the sample is introduced from the sample flow channel and the nucleic acid amplification reagent is introduced from the nucleic acid amplification reagent flow channel into the coupling portion into which the water-insoluble solvent has been introduced. Then, for example, the water-insoluble solvent, the sample, and the nucleic acid amplification reagent are brought into contact with one another in the coupling portion, and the mixture thereof is emulsified and delivered from the coupling portion to the delivery flow channel as the emulsion. As to the sample and the nucleic acid amplification reagent, for example, one of them may be contained in the water-insoluble solvent and the other may be contained in the water-soluble solvent, or both of them may be contained in one of the water-insoluble solvent and the water-soluble solvent. The nucleic acid amplification reagent may be, as described above, contained in the sample. In this case, the emulsion can be formed in the same manner as described above using an emulsifying device provided with a sample flow channel, a water-insoluble solvent flow channel, a coupling portion, and a delivery flow channel delivered from the coupling portion, for example.

Examples of the water-insoluble solvent include oil, mineral oil, chloroform, and aromatic compounds. One of the water-insoluble solvents may be used alone or two or more of them may be used in combination.

Examples of the water-soluble solvent include water, buffer solutions, and water-soluble polymer solutions. One of the water-soluble solvents may be used alone or two or more of them may be used in combination.

In the step (1-1), the volume ratio (N:A) of a water-insoluble solvent (N) and a water-soluble solvent (A) to be brought into contact with each other is, for example, 1:0.00001 to 2, 1:0.0001 to 1, or 1:0.001 to 0.5.

The emulsion formed in the step (1-1) is, for example, a water-in-oil (W/O type) emulsion. The average volume of the drop in the emulsion is, for example, 0.0001 to 50000 nL, 0.001 to 500 nL, or 0.01 to 50 nL. The number of drops in the emulsion is not limited as long as it is more than one, and is, for example, 2 to 1000000000, 1000 to 1000000000, or 10000 to 1000000000. The concentrations of the template nucleic acid and the nucleic acid amplification reagent contained in the drop are not particularly limited. The concentration of the template nucleic acid in the drop is, for example, 0 to 5000 µg/L, 0 to 500 µg/L, or 0 to 50 µg/L.

Step (1-2)

In the step (1-2), the sample is fractionated into the plurality of template nucleic acid fractions by dispensing the sample to a chip provided with a plurality of fraction formation portions on its surface. The chip used in the step (1-2) can be any chip as long as it is provided with a plurality of fraction formation portions on its surface. The specific examples of the chip include the following chip (A), chip (B), and chip (C). Hereinafter, the step (1-2) is referred to as step (1-2A) when the chip (A) is used, the step (1-2) is referred to as step (1-2B) when the chip (B) is used, and the step (1-2) is referred to as step (1-2C) when the chip (C) is used.

(A) A chip in which the surface of the template nucleic acid fraction formation portion is hydrophilic and the surface of the region excluding the template nucleic acid fraction formation portion is hydrophobic.

(B) A chip in which the template nucleic acid fraction formation portion is a dent of the surface of the chip, and a region excluding the template nucleic acid fraction formation portion is a non-dent.

(C) A chip in which the template nucleic acid fraction formation portion is a dent of the chip and the inner surface of the template nucleic acid fraction formation portion is hydrophilic, and a region excluding the template nucleic acid fraction formation portion is a non-dent and the surface of the region excluding the template nucleic acid fraction formation portion is hydrophobic.

Step (1-2A)

The step (1-2A) is a step of using the chip (A). In the chip (A), the surface of the fraction formation portion is hydrophilic and the surface of the region excluding the fraction formation portion is hydrophobic. Thus, by applying the sample to the surface of the chip, the sample is separated into the hydrophilic template nucleic acid fraction formation portions, so that the sample can be fractionated into the plurality of template nucleic acid fractions.

In the chip (A), the fraction formation portion can be formed by applying a solvent containing a hydrophilic substance and a solvent containing a hydrophobic substance to the substrate of the chip, for example. When the substrate is hydrophilic or hydrophobic, the fraction formation portion can be formed by applying the solvent containing a hydrophobic substance or the solvent containing a hydrophilic substance to the substrate. The hydrophilic substance and the hydrophobic substance are not particularly limited and publicly known substances can be used. In the chip (A), the number of the fraction formation portions is not particularly limited as long as it is more than one. When there is a plurality of fraction formation portions, the distance between the fraction formation portions can be determined appropriately according to the size of each template nucleic acid fraction, for example. Specifically, the distance can be a distance with which the template nucleic acid fractions are not in contact among one another.

Step (1-2B)

The step (1-2B) is a step of using the chip (B). In the chip (B), the template nucleic acid fraction formation portion is a dent of the surface of the chip and the region excluding the template nucleic acid fraction formation portion is a non-dent. Thus, by applying the sample to the surface of the chip, the sample is introduced into the template nucleic acid fraction formation portions, which are dents on the chip, so that the sample can be fractionated into the plurality of template nucleic acid fractions.

In chip (B), the fraction formation portion can be formed by cutting the substrate of the chip, for example. In the chip (B), the number of the fraction formation portions is not particularly limited as long as it is more than one. The inner product of the fraction formation portion is not particularly limited and can be determined appropriately according to the average volume of the template nucleic acid fractions, for example.

Step (1-2C)

The step (1-2C) is a step of using the chip (C). In the chip (C), the template nucleic acid fraction formation portion is a dent of the chip and the inner surface of the template nucleic acid fraction formation portion is hydrophilic, and the region excluding the template nucleic acid fraction formation portion is a non-dent and the surface of the region excluding the template nucleic acid fraction formation portion is hydrophobic. Thus, by applying the sample to the surface of the chip, the sample is separated into the hydrophilic template nucleic acid fraction formation portions, so that the sample can be fractionated into the plurality of template nucleic acid fractions. The chip (C) can fractionate the sample into the plurality of template nucleic acid fractions promptly and accurately owing to the combination of the dent and hydrophilicity in the fraction formation portions and the combination of the non-dent and hydrophobicity in the region excluding the fraction formation portions.

Regarding the formation method, the number, and the inner products of the fraction formation portions of the chip (C), reference can be made to the descriptions as to the chip (A) and the chip (B).

In the step (1-2), the nucleic acid amplification reagent may be arranged in the template nucleic acid fraction formation portion of the chip, and the template nucleic acid fraction may be caused to contain the nucleic acid amplification reagent in the template nucleic acid fraction formation portion on the chip in the fractionation step. The number of the chips used in the step (1-2) is not particularly limited and can be determined appropriately according to the number of the template nucleic acid fractions to be fractionated in the fractionation step. Specifically, the number of the chips used in the step (1-2) may be one or more than one.

2. Amplification Step

In the amplification step, the target sequence and its complementary sequence in the template nucleic acid are amplified in the presence of the nucleic acid reagent with respect to each of the plurality of template nucleic acid fractions. Specifically, the amplification step is conducted by subjecting the water-insoluble solvent to a nucleic acid amplification reaction condition. Thereby, the target sequence and its complementary sequence in the template nucleic acid are amplified from each of the first primer and the second primer with respect to the template nucleic acid fraction containing the template nucleic acid and the nucleic acid amplification reagent among the plurality of template nucleic acid fractions.

In the analysis method of the present invention, the amplification method adopted in the amplification step can be, for example, an isothermal amplification method and a non-isothermal amplification. The isothermal amplification method can be, for example, a SmartAmp method (NATURE METHODS (2007) VOL. 4 NO. 3 p 257, Japanese Patent No. 3897805), a strand displacement amplification (SDA) method (JP H7 (1995)-114718 B), a modified SDA method (U.S. Pat. No. 5,824,517, WO 99/09211, WO 95/25180), a nucleic acid sequence amplification (NASBA) method (Japanese Patent No. 2650159), a loop-mediated isothermal amplification (LAMP) method (Japanese Patent No. 3313358, Nucleic Acids Research, 2000, Vol. 28, No. 12, e63), an isothermal and chimeric primer-initiated amplification of nucleic acids (ICAN) (WO 02/16639), a self-sustained sequence replication (3SR) method, a transcription-mediated amplification (TMA) method, an invader method, and a rolling cycle amplification (RCA) method. The steps and conditions of the isothermal amplification are not particularly limited and the steps and conditions of conventional isothermal amplification reactions can be adopted. The non-isothermal amplification method can be, for example, a PCR method. The steps and conditions of the non-isothermal amplification are not particularly limited and the steps and conditions of conventional non-isothermal amplification reactions can be adopted. Furthermore, as described below, for example, in the case of analyzing the methylation of the template nucleic acid, the hydroxymethylation of the template nucleic acid, or the like, the amplification method can be, for example, an end-specific PCR (ESPCR) method, a helper-dependent chain reaction (HDCR) method, and the like. The steps and conditions of the ESPCR method and the HDCR method are not particularly limited and conventional steps and conditions can be adopted.

As described above, the amplification method of the present invention may further include the step of generating cDNA from RNA by reverse transcription when the template nucleic acid in the amplification step is cDNA, for example. In this case, for example, the RNA is a template nucleic acid of the reverse transcription in the reverse transcription step and cDNA obtained in the reverse transcription step is a template nucleic acid for the amplification reaction in the amplification step. The RNA can be, as described above, RNA contained in the organism sample, for example.

3. Detection Step

In the detection step, the generation or the quenching of a signal that shows an amplification of the target sequence or the complementary sequence is detected with respect to the plurality of fractions, after the amplification step. The kind of the signal is not particularly limited and can be determined appropriately according to the kind of the signal generating substance. Examples of the kind of the signal include fluorescence and luminescence. In the detection step, for example, the degree of the amplification can be detected by measuring a signal intensity. The specification of the present invention is described below with reference to a fluorescence signal as the signal, unless otherwise noted. The present invention, however, is not limited thereto, and the "fluorescence signal" can be replaced with a "luminescence signal", for example.

In the detection step, as described above, the detection of the signal that shows the amplification may be, for example, the detection of the amplified product obtained using the primer or the detection of association of the amplified product and the probe or dissociation of the associate. In the former case, the detection of a signal can be, for example, the detection of the formation or the dissociation of a double-strand structure. The method of detecting the formation or the dissociation of a double-strand structure is not particularly limited. In the latter case, the detection of the signal that shows the amplification can be, for example, the detection of the association of the probe and the amplified product or the dissociation of the associate in accordance with the temperature change, the pH change, the concentration change or salt concentration change of a denaturant. Generally, it has been known that a pair of single-stranded nucleic acids having the sequences complementary to each other associate (formation of double-strand structure) or dissociates (dissociation from double-strand structure to single stranded structure) in accordance with the above-described changes. In the detection step, the method of detecting the association or the dissociation of the associate in accordance with the temperature change, the pH change, and the concentration change or salt concentration change of a denaturant is not particularly limited, and can be, for example, a detection method conducted by a melting curve analysis.

In the detection step, the method of detecting the signal with respect to the plurality of template nucleic acid fractions is not particularly limited and can be determined appropriately according to the kind of the signal. The detection method can be, for example, the detection using a flow cytometer, a fluorescence microscope, a fluorescence spectrometer, or the like. Furthermore, the detection method may be a highly accurate detection method that allows the fluorescence intensity per molecule in the template nucleic acid fraction to be analyzed, as it increases the detection sensitivity of the signal and allows the template nucleic acid to be analyzed more accurately. Examples of the highly accurate detection method include fluorescence correlation spectroscopy (FCS), fluorescence intensity distribution analysis (FIDA), FIDA polarization (FIDA-PO), and scanning single-molecule counting (SSMC).

When the fractionation step is the step (1-1), the generation or quenching of a signal is detected with respect to the drop in the emulsion in the detection step. The detection method of the signal is not particularly limited, and can be, for example, a method of detecting an emulsion that passes through a flow channel, a method of detecting an emulsion after developing it into a planar shape, and the like.

In the case of detecting the emulsion passing through the flow channel, preferably, the emulsion is caused to pass through a flow channel, and the generation or quenching of a signal is detected with respect to the drop at a predetermined site of the flow channel when the drop in the emulsion passes through the flow channel. In the flow channel, the predetermined site can be set at any position. There are no particular limitations on the shape and the length of the flow channel. The inner diameter of the flow channel is not particularly limited, and can be, for example, the mean diameter of the drop. The flow channel may have a fixed inner diameter as a whole or may partially have different inner diameters, for example. The flow channel may be, for example, a flow channel having an inner diameter at the predetermined site that allows the drops to be passed at least one by one. By designing the flow channel having such an inner diameter, for example, each of the plurality of drops can be detected at the predetermined site, which allows a template nucleic acid to be analyzed more accurately.

Furthermore, in the case of detecting the emulsion passing through the flow channel, drops in each of which the amplification has been detected (amplified fractions) may be recovered by the recovery step in the detection step of the analysis method of the present invention. In the recovery step, drops in each of which the amplification has not been detected may be also recovered. Specifically, in the case of recovering drops in each of which the amplification has been detected and drops in each of which the amplification has not been detected in the detection step, the flow channel includes, from the upstream side toward the downstream side, a first flow channel and a second flow channel and a third flow channel that are diverged from the end of the first flow channel at the downstream side. The first flow channel is a flow channel through which the water-insoluble solvent subjected to the detection step passes, the second flow channel is a flow channel through which the drops in each of which the amplification has been detected in the detection step pass, and the third flow channel is a flow channel through which the drops in each of which the amplification has not been detected in the detection step pass. Furthermore, the first flow channel includes the predetermined site at its downstream-side terminal region and a recovery step at which the drops in each of which the amplification has been detected and the drops in each of which the amplification has not been detected are recovered. In the detection step, the drops passing through the predetermined site of the first flow channel are introduced into the second flow channel by the recovery step upon the detection of amplification and introduced into the third flow channel by the recovery step upon the detection of no amplification. The first analysis method with the flow channel having such a structure can recover the drops in each of which the amplification has been detected and the drops in each of which the amplification has not been detected by the recovery step. Thus, for example, the drops in each of which the amplification has been detected can be reanalyzed, which allows a template nucleic acid to be analyzed more accurately. In the downstream terminal region, it is only required that the predetermined site and the recovery step are disposed so that the recovery step can recover the drops based on the detection of the amplification in the drop. For example, in the downstream terminal region, the predetermined site is disposed at the upstream side of the first flow channel relative to the recovery step.

In the detection step, the method of recovering drops in each of which the amplification has been detected and drops in each of which the amplification has not been detected is not particularly limited and a publicly known droplet recovery method can be adopted. Examples of the recovery method include a method of recovering the drops by sucking and a method of recovering the drops by charging. In the recovery step, for example, the drops may be charged positively or negatively. In the case of recovering the drops by charging, the recovery step can be, for example, a charging unit that charges the drops to be introduced into the first flow channel or the drops that have been introduced into the first flow channel. In the latter case, the recovery step can be, for example, a charging unit that charges the drops that have been passed through the predetermined site. In this case, the second flow channel has either one of a positive electrode and a negative electrode and the third flow channel has the other. In the detection step, when the amplification of the drop that has been passed through the predetermined site of the first flow channel is detected, the drop is charged in reverse of the polarity of the second flow channel and introduced into the second flow channel by the recovery step. In the detection step, when the amplification of the drop that has been passed through the predetermined site of the first flow channel is not detected, the drop is charged in reverse of the polarity of the third flow channel and introduced into the third flow channel by the recovery step. In the recovery step, the drop may be charged either positively or negatively. In this case, the second flow channel and the third flow channel each have an electrode to be charged positively or a negatively. When the amplification of the drop that has been charged by the recovery step and passed through the predetermined site of the first flow channel is detected, the second flow channel is charged in reverse of the polarity of the drop and the drop is introduced into the second flow channel. When the amplification of the drop that has been charged by the recovery step and passed through the predetermined site of the first flow channel is not detected, the third flow channel is charged in reverse of the polarity of the drop and the drop is introduced into the third flow channel.

In the case of detecting the signal by developing the emulsion into a planar shape, preferably, the detection step obtains the image of drops in the emulsion that has been developed into a planar shape. The image of drops can be obtained, for example, by a publicly known imaging unit such as a fluorescence microscope.

When the fractionation step is the step (1-2), the image of the plurality of template nucleic acid fractions on at least one chip is obtained in the detection step. The image of the plurality of template nucleic acid fractions can be obtained, for example, by the above-described imaging unit.

When the sample contains at least two template nucleic acids, in the detection step, the generation or quenching of a signal that shows the amplification may be detected separately with respect to each of the template nucleic acids, the generation or quenching of a signal may be detected simultaneously with respect to some of the template nucleic acids and separately with respect to the rest of the template nucleic acids, or the generation or quenching of a signal may be detected simultaneously with respect to all of the template nucleic acids. Specifically, when the sample contains at least two template nucleic acids, for example, the amplification of each of the template nucleic acids can be detected by detecting the signal generating substance that generates or quenches a signal with respect to each of the template nucleic acids.

When the nucleic acid amplification reagent contains a non-fluorogenic probe, in the detection step, the amplification of the template nucleic acid can be detected by detecting the generation or quenching of a signal of the non-fluorogenic probe, for example.

In the present invention, for example, the detection step may be conducted during the amplification step. In this case, the generation or quenching of a signal may be detected at least once over time in the amplification step, for example.

4. Discrimination Step

In the discrimination step, a template nucleic acid fraction in which the generation or quenching of a signal that shows the amplification has been detected among the plurality of template nucleic acid fractions is discriminated as an amplified fraction in which the target sequence or the complementary sequence has been amplified. The discrimination step may be performed based on the presence or absence of a signal or the intensity of a signal, for example. In the latter case, the threshold of the signal intensity is set, and the template nucleic acid fraction in which the signal intensity equal to or more than the threshold or the signal intensity equal to or less than the threshold has been detected is discriminated as the amplified fraction, for example. As a specific example, when a signal is generated by the amplification, the template nucleic acid fraction in which the signal intensity equal to or more than the threshold has been detected is discriminated as the amplified fraction and the template nucleic acid fraction in which the signal intensity less than the threshold has been detected is not discriminated as the amplified fraction.

When the image of drops is obtained in the detection step, the discrimination step discriminates the drop in the emulsion in which the generation or quenching of a signal has been detected in the image as the amplified fraction. In the detection step, when the image of the plurality of template nucleic acid fractions is obtained, the discrimination step discriminates the template nucleic acid fraction on the chip in which the generation or quenching of a signal has been detected in the image as the amplified fraction. The discrimination may be performed based on the presence or absence of a signal or the intensity of a signal, for example.

When the sample contains at least two template nucleic acids, the discrimination step may discriminate a template nucleic acid fraction in which the amplification of one template nucleic acid has been detected as the amplified fraction, discriminate a template nucleic acid fraction in which the amplification of at least two template nucleic acids has been detected as the amplified fraction, or discriminate a template nucleic acid fraction in which the amplification of all the template nucleic acids has been detected as the amplified fraction.

When the nucleic acid amplification reagent contains a non-fluorogenic probe, for example, the discrimination step may discriminate a template nucleic acid fraction in which the amplification of the template nucleic acid has been detected as the amplified fraction by detecting the generation or quenching of a signal of the non-fluorogenic probe.

In the analysis method of the present invention, the combination of the signal generating substance, the fractionation step, and the amplification step is not particularly limited, and can be, for example, the combinations (i) to (xii) shown in the following Table 1. In Table 1, the signal generating substance, the fractionation step, and the amplification step adopted in the combinations (i) to (xii) are indicated with "open circles (○)".

TABLE 1

| | | (i) | (ii) | (iii) | (iv) | (v) | (vi) |
|---|---|---|---|---|---|---|---|
| Signal generating substance | Signal generating binding substance | ○ | ○ | ○ | ○ | | |
| | Signal primer | | | | | ○ | ○ |
| Fractionation step | step (1-1) | ○ | ○ | | | ○ | ○ |
| | step (1-2) | | | ○ | ○ | | |
| Amplification step | Non-isothermal amplification method | ○ | | ○ | | ○ | |
| | Isothermal amplification method | | ○ | | ○ | | ○ |

| | | (vii) | (viii) | (ix) | (x) | (xi) | (xii) |
|---|---|---|---|---|---|---|---|
| Signal generating substance | Signal generating binding substance | | | ○ | ○ | ○ | ○ |
| | Signal primer | ○ | ○ | ○ | ○ | ○ | ○ |
| Fractionation step | step (1-1) | | | ○ | ○ | | |
| | step (1-2) | ○ | ○ | | | ○ | ○ |
| Amplification step | Non-isothermal amplification method | ○ | | ○ | | ○ | |
| | Isothermal amplification method | | ○ | | ○ | | ○ |

When the template nucleic acid is a template nucleic acid complex containing the target substance and the binding substance, the analysis method of the present invention may include the step of forming a template nucleic acid complex by bringing a sample containing the target substance into contact with a binding substance labeled with the template nucleic acid prior to the fractionation step. Furthermore, when the template nucleic acid is a template nucleic acid complex containing the target substance and the binding substance, for example, determination of the presence or absence of the target substance (qualitative analysis), determination of the quantity of the target substance (quantitative analysis), and the like may be performed based on the result obtained in the determination step described below.

In the analysis method of the present invention, for example, the generation or quenching of a signal that shows an amplification of the target sequence or the complementary sequence may be detected with respect to each of the plurality of template nucleic acid fractions before the amplification step, and a template nucleic acid fraction in which the generation or quenching of a signal that shows the amplification has been detected among the plurality of template nucleic acid fractions may be discriminated as an amplified fraction in which the target sequence or the complementary sequence has been amplified by comparing the signal detected before the amplification step and the signal detected after the amplification step in the discrimination step. Furthermore, in the analysis method of the present invention, generation or quenching of a signal that shows an amplification of the target sequence or the complementary sequence may be detected with respect to each of the plurality of template nucleic acid fractions before the fractionation step, and a template nucleic acid fraction in which the generation or quenching of a signal that shows the amplification has been detected among the plurality of template nucleic acid fractions may be discriminated as an amplified fraction in which the target sequence or the complementary sequence has been amplified by comparing the signal detected before the fractionation step and the signal detected after the amplification step in the discrimination step. According to the analysis method of the present invention, for example, the influence of the background in the discrimination can be avoided by discriminating the amplified fraction in the discrimination step using the signal detected before the fractionation step or before the amplification step, which allows the template nucleic acid to be analyzed more accurately. Specifically, in the case where a signal is generated by the amplification and the discrimination is performed by setting the threshold of the signal intensity, the discrimination can by performed using the signal intensity difference obtained by subtracting the signal intensity detected before the amplification step or the signal intensity detected before the fractionation step from the signal intensity detected after the amplification step. More specifically, the template nucleic acid fraction in which a signal intensity difference is equal to or more than the threshold is discriminated as the amplified fraction and the template nucleic acid fraction in which the signal intensity difference is less than the threshold is not discriminated as the amplified fraction.

In the analysis method of the present invention, the combination of the signal generating substance, the fractionation step, the amplification step, and the detection step is not particularly limited, and can be, for example, the combinations (i-1) to (xii-3) shown in the following Table 2. In Table 2, the signal generating substance, the fractionation step, the amplification step, and the detection step adopted in the combinations (i-1) to (xii-3) are indicated with "open circles (○)".

The analysis method of the present invention may further include the step of conducting an analysis by a melting curve analysis after the detection step, for example. According to the analysis method of the present invention, for example, the amplification of the target sequence or the complementary sequence can be analyzed more specifically and accurately by combining a fluorogenic signal generating substance and the analysis step conducted by a melting curve analysis, which allows the template nucleic acid to be analyzed more accurately.

The analysis method of the present invention may further include, after the discrimination step, the step of recovering the amplified fraction in which the amplification of the target sequence or the complementary sequence has been detected in the discrimination step, for example. In the analysis method of the present invention, owing to the recovery step, for example, the amplified fraction in which amplification has been detected can be reanalyzed, which allows a template nucleic acid to be analyzed more accurately. The recovery step can be performed, for example, by the recovery unit.

In the discrimination step, when the amplification of the target sequence or the complementary sequence is discriminated based on the image of drops, the recovery step recovers the drop that has been discriminated as the amplified fraction from the emulsion developed into a planar

TABLE 2

| | | (i-1) | (i-2) | (i-3) | (ii-1) | (ii-2) | (ii-3) | (iii-1) | (iii-2) | (iii-3) | (iv-1) | (iv-2) | (iv-3) |
|---|---|---|---|---|---|---|---|---|---|---|---|---|---|
| Signal generating substance | Signal generating binding substance | ○ | ○ | ○ | ○ | ○ | ○ | ○ | ○ | ○ | ○ | ○ | ○ |
| | Signal primer | | | | | | | | | | | | |
| Fractionation step | step (1-1) | ○ | ○ | ○ | ○ | ○ | ○ | | | | | | |
| | step (1-2) | | | | | | | ○ | ○ | ○ | ○ | ○ | ○ |
| Amplification step | Non-isothermal amplification method | ○ | ○ | ○ | | | | ○ | ○ | ○ | | | |
| | Isothermal amplification method | | | | ○ | ○ | ○ | | | | ○ | ○ | ○ |
| Detection step | Before fractionation step | | | ○ | | | ○ | | | ○ | | | ○ |
| | Before amplification step | | ○ | | | ○ | | | ○ | | | ○ | |
| | After amplification step | ○ | ○ | ○ | ○ | ○ | ○ | ○ | ○ | ○ | ○ | ○ | ○ |

| | | (v-1) | (v-2) | (v-3) | (vi-1) | (vi-2) | (vi-3) | (vii-1) | (vii-2) | (vii-3) | (viii-1) | (viii-2) | (viii-3) |
|---|---|---|---|---|---|---|---|---|---|---|---|---|---|
| Signal generating substance | Signal generating binding substance | | | | | | | | | | | | |
| | Signal primer | ○ | ○ | ○ | ○ | ○ | ○ | ○ | ○ | ○ | ○ | ○ | ○ |
| Fractionation step | step (1-1) | ○ | ○ | ○ | ○ | ○ | ○ | | | | | | |
| | step (1-2) | | | | | | | ○ | ○ | ○ | ○ | ○ | ○ |
| Amplification step | Non-isothermal amplification method | ○ | ○ | ○ | | | | ○ | ○ | ○ | | | |
| | Isothermal amplification method | | | | ○ | ○ | ○ | | | | ○ | ○ | ○ |
| Detection step | Before fractionation step | | | ○ | | | ○ | | | ○ | | | ○ |
| | Before amplification step | | ○ | | | ○ | | | ○ | | | ○ | |
| | After amplification step | ○ | ○ | ○ | ○ | ○ | ○ | ○ | ○ | ○ | ○ | ○ | ○ |

| | | (ix-1) | (ix-2) | (ix-3) | (x-1) | (x-2) | (x-3) | (xi-1) | (xi-2) | (xi-3) | (xii-1) | (xii-2) | (xii-3) |
|---|---|---|---|---|---|---|---|---|---|---|---|---|---|
| Signal generating substance | Signal generating binding substance | ○ | ○ | ○ | ○ | ○ | ○ | ○ | ○ | ○ | ○ | ○ | ○ |
| | Signal primer | ○ | ○ | ○ | ○ | ○ | ○ | ○ | ○ | ○ | ○ | ○ | ○ |
| Fractionation step | step (1-1) | ○ | ○ | ○ | ○ | ○ | ○ | | | | | | |
| | step (1-2) | | | | | | | ○ | ○ | ○ | ○ | ○ | ○ |
| Amplification step | Non-isothermal amplification method | ○ | ○ | ○ | | | | ○ | ○ | ○ | | | |
| | Isothermal amplification method | | | | ○ | ○ | ○ | | | | ○ | ○ | ○ |
| Detection step | Before fractionation step | | | ○ | | | ○ | | | ○ | | | ○ |
| | Before amplification step | | ○ | | | ○ | | | ○ | | | ○ | |
| | After amplification step | ○ | ○ | ○ | ○ | ○ | ○ | ○ | ○ | ○ | ○ | ○ | ○ | shape. Furthermore, in the discrimination step, when the amplification of the target sequence or the complementary sequence is discriminated based on the image of the plurality of template fractions, the recovery step recovers the template nucleic acid fraction that has been discriminated as the amplified fraction from the chip. In the recovery step, for example, a publicly known solution recovery apparatus and the like can be used.

When the analysis method of the present invention includes the recovery step, preferably, the analysis method further includes the step of amplifying the target sequence and the complementary sequence in the template nucleic acid with respect to the amplified fraction. This amplification is referred to as a second amplification step. In the analysis method of the present invention, owing to the second amplification step, for example, the signal of the amplified fraction can be amplified, which allows a template nucleic acid to be analyzed more accurately. The second amplification step can be conducted in the same manner as the amplification step, for example.

The analysis method of the present invention may further include the step of determining the template nucleic acid based on the detection result obtained in the detection step, for example. Note that, the determination of the template nucleic acid is not particularly limited, and examples thereof include the determination of the presence or absence of the template nucleic acid (qualitative analysis), the determination of the quantity of the template nucleic acid (quantitative analysis), and the determination of the type of the base of the nucleic acid mutation site in the template nucleic acid (typing) as described above. When the sample contains at least two template nucleic acids, one template nucleic acid may be determined, at least two template nucleic acids may be determined, or all the template nucleic acids may be determined in the template nucleic acid determination step. Furthermore, when the nucleic acid amplification reagent contains a non-fluorogenic probe, for example, the template nucleic acid may be determined based on the detection result obtained using the non-fluorogenic probe in addition to the detection result obtained using the signal generating substance. Moreover, when generation or quenching of a signal that shows the amplification has been detected before the fractionation step or before the amplification step, the template nucleic acid may be determined in the determination step based on the signal detected before the fractionation step and the signal detected in the detection step after the amplification step.

In the analysis method of the present invention, pretreatment may be applied to the template nucleic acid contained in the sample according to the purpose of the analysis, for example. The pretreatment may be performed before the amplification step, specifically prior to the fractionation step, or may be performed after the fractionation step and before the amplification step, for example. In the latter case, for example, a reagent required for the pretreatment may be introduced into the fraction. Preferably, the pretreatment is performed prior to the fractionation step, for example. That is, in the analysis method of the present invention, preferably, after application of the pretreatment to the template nucleic acid contained in the sample, the fractionation step is performed and subsequently the amplification step is performed.

In the case of analyzing the modification of the template nucleic acid by the analysis method of the present invention, preferably, pretreatment is applied to the template nucleic acid in the pretreatment step. Examples of the modification include methylation and hydroxymethylation. In the case of analyzing the modification of the template nucleic acid, examples of the pretreatment include the following methods (1) to (3):

(1) pretreatment of converting a non-modified base X or a modified base X in the template nucleic acid into another base Y;
(2) pretreatment of enriching a modified template nucleic acid using a binding substance that binds to a modified nucleic acid; and
(3) pretreatment of cleaving a non-modified region or a modified region.

In the case of the method (1), for example, when if X at a specific site in a template nucleic acid is not modified, the specific site is converted into base Y, and if base X at the specific site is modified, the specific site is not converted into base Y. Alternatively, for example, if base X at a specific site in a template nucleic acid is modified, the specific site is converted into base Y, and if base X at the specific site is not modified, the specific site is not converted into base Y. Accordingly, the modification in a template nucleic acid can be analyzed based on the difference in conversion.

In the case of the method (2), for example, a modified template nucleic acid among template nucleic acids can be enriched using a binding substance that binds to a nucleic acid in which base X at a specific site is modified by binding the binding substance to a modified template nucleic acid. Using the enriched template nucleic acid, the modification in a template nucleic acid can be analyzed.

In the case of the method (3), for example, in the case of cleaving a non-modified region, a modified template nucleic acid is not cleaved and a non-modified template nucleic acid is cleaved, and in the case of cleaving a modified region, a modified template nucleic acid is cleaved and a non-modified template nucleic acid is not cleaved. Furthermore, for example, in the case of cleaving a modified region, a non-modified template nucleic acid is not cleaved and a modified template nucleic acid is cleaved, and in the case of cleaving a non-modified region, a non-modified template nucleic acid is cleaved and a modified template nucleic acid is not cleaved. The modification in a template nucleic acid can be analyzed based on whether the template nucleic acid has been cleaved.

First, as a specific example, an example of the pretreatment in the case of analyzing the methylation of a template nucleic acid is described.

In the case of the method (1), preferably, a non-methylated cytosine residue of the template nucleic acid is converted into a uracil residue or a uracil derivative residue (hereinafter, also referred to as converted residue) in the pretreatment step, for example. The reagent used for the conversion treatment is not limited to particular reagents, and can be, for example, bisulfite and the like. The steps following the pretreatment step are not particularly limited, and reference can be made to the above description. Specific examples of the step are as follows: a melting curve analysis may be performed as the detection step after the amplification step, for example; and the detection step may be performed in the amplification step after conducting the multiplex nucleic acid amplification to a template nucleic acid having a methylcytosine residue and a template nucleic acid having a converted residue, for example.

In the case of the method (3), preferably, a non-methylated region or a methylated region of the template nucleic acid is cleaved in the pretreatment step, for example. The reagent used for the cleavage is not limited to particular reagents, and can be, for example, a restriction enzyme. As the restriction enzyme, for example, a methylation-sensitive restriction enzyme that can cleave a predetermined sequence if it is not methylated and cannot cleave a predetermined sequence if it is methylated, a methylation-dependent restriction enzyme that can cleave a predetermined sequence if it is methylated, and the like can be used. As the restriction enzyme, for example, one of or both of the methylation-sensitive restriction enzyme and the methylation-dependent restriction enzyme can be used. In the case of cleaving the non-methylated region, preferably, the restriction enzyme is a restriction enzyme that cleaves a non-methylated region more effectively than a methylated region and is dependent on a non-methylated region (or is sensitive to a methylated region), for example. In the case of cleaving the methylated region, preferably, the restriction enzyme is a restriction enzyme that cleaves a methylated region more effectively than a non-methylated region and is dependent on a methylated region (or is sensitive to a non-methylated region), for example. Examples of the methylcytosine-sensitive restriction enzyme include AatII, ApaI, and BstUI. Examples of the methylcytosine-dependent restriction enzyme include MspJI and GlaI. The steps following the pretreatment step are not particularly limited, and reference can be made to the above description. Specific examples of the step are as follows: the detection step may be performed, for example, after performing the ESPCR method, the HDCR method, and the amplification method using a chimera primer and a blocker as the amplification step; and the detection step may be performed after performing the multiplex nucleic acid amplification in the amplification step, for example. In the present invention, in the case of analyzing the methylation using the cleavage of a non-methylated region or a methylated region, for example, reference can be made to the following research papers. Sensitive measurement of unmethylated repeat DNA sequences by end-specific PCR, Keith N. Rand et al., BioTechniques 2010, 49(4) Sensitive and selective amplification of methylated DNA sequences using helper-dependent chain reaction in combination with a methylation-dependent restriction enzymes, Keith N. Rand et al., Nucleic Acids Research, 2013, 41(1), e15

Furthermore, the multiplex nucleic acid amplification to a template nucleic acid having a methylcytosine residue and a template nucleic acid having a converted residue may be performed in the amplification step, for example.

In the case of the method (2), preferably, a methylated template nucleic acid is enriched in the pretreatment step, for example. The method of enriching the methylated template nucleic acid is not limited to particular methods, and the methylated template nucleic acid may be enriched, using the binding substance that binds to a methylated template nucleic acid, by binding the binding substance to the methylated template nucleic acid, for example. Examples of the binding substance include methylated DNA-binding protein and anti-methylcytosine antibody. The methylated DNA-binding protein can be, for example, MECP2 and the like. The steps following the pretreatment step are not particularly limited, and reference can be made to the above description. Specific examples of the step are as follows: the melting curve analysis may be performed in the detection step after the amplification step, for example; and the detection step may be performed after performing the multiplex nucleic acid amplification in the amplification step, for example. In the present invention, in the case of analyzing the methylation using the methylated DNA-binding protein, for example, Methylated CpG Island Recovery Assay (MIRA) may be performed. Furthermore, in the present invention, in the case of analyzing the methylation using the anti-methylcytosine antibody, for example, Methylated DNA Immunoprecipitation (MeDIP) may be performed.

Next, as a specific example, an example of the pretreatment in the case of analyzing the hydroxymethylation of a template nucleic acid is described.

In the case of the method (1), preferably, the hydroxymethyl cytosine residue in the template nucleic acid is converted into a non-hydroxymethylated base residue in the pretreatment step, for example. The hydroxymethylcytosine can be, for example, a 5-hydroxymethylcytosine residue. The non-hydroxymethylated base residue can be, for example, a thymine residue, a thymine derivative residue, a uracil residue, or a uracil derivative residue (hereinafter, also referred to as a converted residue). The reagent used for the conversion treatment is not limited to particular reagents. As a specific example, in the case of converting into a thymine residue or a thymine derivative residue, for example, a tungsten oxidizing agent or the like can be used. The tungsten oxidizing agent can be, for example, a peroxotungsten binuclear complex. Furthermore, in the case of converting into a uracil residue or a uracil derivative residue, for example, potassium perruthenate ($KRuO_4$) and bisulfite can be used in combination. The steps following the pretreatment step are not particularly limited, and reference can be made to the above description. Specific examples of the step are as follows: the melting curve analysis may be performed as the detection step after the amplification step, for example; and the detection step may be performed after performing the multiplex nucleic acid amplification to a template nucleic acid having a methylcytosine residue and a template nucleic acid having a converted residue in the amplification step, for example. In the present invention, in the case of analyzing the hydroxymethylation using a tungsten oxidizing agent, for example, reference can be made to the following research paper.

Chem Commun (Camb). Okamoto A, Sugizaki K, Nakamura A, Yanagisawa H, Ikeda S. 2011; 47(40): 11231-3.

Furthermore, in the present invention, in the case of analyzing the hydroxymethylation using potassium perruthenate ($KRuO_4$) and bisulfite in combination, for example, reference can be made to the following research paper.

Bioorganic & Medical Chemistry Letters. Seketsu Fukuzawa, Kazuo Tachibana, Shoji Tajima, Isao Suetake. 2015, 25, 5667-5671

In the case of the method (3), preferably, the pretreatment step includes the steps of glycosylating a hydroxymethylated region of a hydroxymethylated template nucleic acid; and cleaving the glycosylated region of the hydroxymethylated template nucleic acid, for example. In the glycosylation step, for example, 5-hydroxymethylcytosine (5-hmC) is glycosylated to a glycosylated 5-hmC. The glycosylation can be performed using ß-glycosyl transferase, for example. The reagent used for the cleavage is not limited to particular reagents, and can be, for example, a restriction enzyme. As the restriction enzyme, for example, a glycosylation-sensitive restriction enzyme that can cleave a predetermined sequence if it is not glycosylated and cannot cleave a predetermined sequence if it is glycosylated, a glycosylation-dependent restriction enzyme that can cleave a predetermined sequence if it is glycosylated, and the like can be used. As the restriction enzyme, for example, one of or both of the glycosylation-sensitive restriction enzyme and the glycosylation-dependent restriction enzyme can be used. Preferably, the restriction enzyme is a restriction enzyme that cleaves a glycosylated region more effectively than a non-glycosylated region and a restriction enzyme that is dependent on a glycosylated region (or is sensitive to a glycosylated region), for example. Examples of the glycosylated 5-hmC-sensitive restriction enzyme include MspI, and HaeIII. The steps following the pretreatment step are not particularly limited, and reference can be made to the above description. Specific examples of the step are as follows: the detection step may be performed, for example, after performing the ESPCR method, the HDCR method, and the amplification method using a chimera primer and a blocker as the amplification step; and the detection step may be performed after performing the multiplex nucleic acid amplification in the amplification step, for example. Furthermore, in the amplification step, for example, the multiplex nucleic acid amplification to a template nucleic acid having a methylcytosine residue and a template nucleic acid having a converted residue may be performed.

In the case of the method (2), preferably, the pretreatment step includes the steps of glycosylating a hydroxymethylated region of a hydroxymethylated template nucleic acid; and enriching the glycosylated hydroxymethylated template nucleic acid, for example. Regarding the glycosylation step, for example, reference can be made to the description as to the method (3). The method of enriching the glycosylated hydroxymethylated template nucleic acid is not limited to particular methods, and the glycosylated hydroxymethylated template nucleic acid may be enriched, using the binding substance that binds to a glycosylated hydroxymethylated template nucleic acid, by binding the binding substance to the glycosylated hydroxymethylated template nucleic acid, for example. The binding substance can be, for example, a glycosylated hydroxymethylated DNA-binding protein or antibody. The antibody can be, for example, an anti-glycosylated 5-hmC antibody. The steps following the pretreatment step are not particularly limited, and reference can be made to the above description. Specific examples of the step are as follows: the melting curve analysis may be performed in the detection step after the amplification step, for example; and the detection step may be performed after performing the multiplex nucleic acid amplification in the amplification step, for example.

<Analysis Method for Target Substance>

The method for analyzing a target substance of the present invention, as described above, includes the steps of bringing a sample containing at least one target substance into contact with at least one fluorogenic probe for each target substance in a reaction solution; and detecting the generation or quenching of a signal of the fluorogenic probe in response to binding between the target nucleic acid and the fluorogenic probe. The method for analyzing a target substance of the present invention is characterized in that it includes the steps of bringing a sample containing at least one target substance into contact with at least one fluorogenic probe for each target substance in a reaction solution; and detecting the generation or quenching of a signal of the fluorogenic probe in response to binding between the target nucleic acid and the fluorogenic probe, and other steps and conditions are not particularly limited. Regarding the method for analyzing a target substance of the present invention, for example, reference can be made to the description as to the method for analyzing a template nucleic acid of the present invention, unless otherwise stated. According to the method for analyzing a target substance of the present invention, a target substance can be analyzed accurately.

The target substance is not limited to particular substances, and examples thereof include nucleic acids, proteins, sugar, and lipid. When the target substance is a nucleic acid, the target substance can be also referred to as a target nucleic acid, for example. The target nucleic acid can be, for example, the above-described template nucleic acids. The target substance may be, for example, a target substance in a state where it is bound to a substance that specifically binds to the target substance. The fluorogenic probe can be, for example, the above-described fluorogenic probe. It is only required that a probe that composes the fluorogenic probe is a substance that specifically binds to a target substance as described above, and specific examples of the probe include nucleic acids, antibodies, affibodies, and aptamers. While the present invention is described below with reference to the case where the target substance is a nucleic acid, regarding the target substance, reference can be made to the following description by replacing the "target nucleic acid" with the "target substance".

The amount of the target nucleic acid contained in the reaction solution is not particularly limited, and is, for example, 100 ng or less. The volume of the reaction solution is not particularly limited, and is, for example, 2 nL or less.

The sample and the fluorogenic probe may be brought into contact with each other, for example, by adding the fluorogenic probe to the sample, by adding the sample to the fluorogenic probe, or by adding the fluorogenic probe and the sample to the water-soluble solvent.

The generation of a signal or the quenching of a signal can be detected by the detection method adopted in the detection step of the method for analyzing a template nucleic acid of the present invention, for example. Specific examples of the detection include the detection of brightness or intensity of at least one kind of the signal in the reaction solution and the counting of at least one kind of the signal in the reaction solution on the molecular level of the fluorogenic probe. The counting on the molecular level can be, for example, the above-described highly accurate detection method.

In the contact and the detection, the temperature of the reaction solution is not particularly limited and can be determined appropriately according to the kind of the target nucleic acid and the fluorogenic probe, for example. The temperature of the reaction solution can be controlled in the contact and the detection, for example.

When the target substance is a nucleic acid, for example, the method for analyzing a target substance of the present invention can detect a small amount of the target nucleic acid and does not need to include the step of amplifying the target nucleic acid.

When at least two kinds of target substances are analyzed, at least two kinds of fluorogenic probes for the target nucleic acids may be used, and the method for analyzing a target substance of the present invention may include the step of calculating the concentration ratio or the abundance ratio of each target nucleic acid from a detected signal value of the at least two kinds of fluorogenic probes detected in the detection step. The detected signal value can be, for example the brightness, intensity, and the like of the signal. The method of calculating the concentration or the amount of the target nucleic acid based on the detected signal value is not limited to particular methods, and can be, for example, a method of calculating based on a calibration curve obtained from a standard sample.

When at least two target nucleic acids are analyzed and at least two kinds of target nucleic acids are adjacent to each other, preferably, at least two fluorogenic probes for the target substances are used and the fluorogenic probes each include a signal generating substance having a fluorescence property different from each other and generate or quench a signal in response to binding to different target nucleic acids. In this case, FRET may be utilized or may not be utilized for the generation or quenching of a signal, for example.

<Analysis Kit for Template Nucleic Acid or Target Substance>

The analysis kit for a template nucleic acid or a target substance of the present invention, as described above, achieves the analysis method of the present invention. The analysis kit of the present invention is characterized in that it achieves the analysis method of the present invention, and other composition and conditions are not particularly limited. Regarding the analysis kit for a template nucleic acid or a target substance of the present invention, for example, reference can be made to the description as to the method for analyzing a template nucleic acid of the present invention, unless otherwise stated.

<Analyzer for Template Nucleic Acid or Target Substance>

The analyzer for a template nucleic acid or a target substance of the present invention, as described above, achieves the analysis method of the present invention. The analyzer of the present invention is characterized in that it achieves the analysis method of the present invention, and other composition and conditions are not particularly limited. Regarding the analyzer for a template nucleic acid or a target substance of the present invention, for example, reference can be made to the description as to the method for analyzing a template nucleic acid of the present invention, unless otherwise stated.

EXAMPLES

The examples of the present invention are described below. The present invention, however, is not limited by the examples below. Commercially available reagents were used based on their protocols unless otherwise noted.

Example 1

The fact that a template nucleic acid can be analyzed accurately by the method for analyzing a template nucleic acid of the present invention was confirmed.

(1) DNA Sample

Plasmid DNA having a sequence of a human 309G mutant type MDM2 gene described in the following Reference Document 1 was mixed with RNase Free Water, thereby obtaining a sample solution.

Reference Document 1: Enokida Y et al. "Rapid Detection of SNP (c.309T>G) in the MDM2 Gene by the Duplex SmartAmp Method", PLOS ONE, 2013, Volume 8, Issue 4, e60151

(2) Preparation of Reagent

The reagent was prepared with reference to Reference Document 1 as to the isothermal amplification reaction system for human MDM2 gene 309G mutation detection. Specifically, first, primers were mixed so as to achieve the composition shown in the following Table 3, thereby obtaining a primer mix. In the following primer mix, MDM2.Bf.202-13.M.E8 (Eprimer) is the signal generating substance. Furthermore, components were mixed so as to achieve the composition shown in the following Table 4, thereby preparing a premix in an amount that can prepare a reaction solution of 4.4 times of reaction (14.5 µL×4.4). As shown in the following Table 4, as the premix, two kinds of premixes each were prepared such that a reaction solution contains 375 or 750 copies of template DNA per reaction.

TABLE 3

(Primer mix)

| Primer name | Base sequence | SEQ ID NO. | Concentration (µmol/L) | Mixing ratio |
|---|---|---|---|---|
| MDM2.Tr.238-20.205-11 | 5'-CGCGGGAGGTCAGCGTTCACACTAGTGACCC-3' | 1 | 100 | 8 |
| MDM2.Ff.172-20.m | 5'-ACCTTCTATACCCTCAGAAGGTCGGGAGTTCAGGGTAAAGGT-3' | 2 | 100 | 8 |
| MSM2.Bf.237-15 | 5'-TCGCAGGTGCCTGTC-3' | 3 | 100 | 4 |
| MDM2.Bf.197-12 | 5'-GGCTGCGGGGCC-3' | 4 | 100 | 4 |
| MDM2.Or.262-18 | 5'-CAATCCCGCCCAGACTAC-3' | 5 | 100 | 1 |
| Distilled water | | | | 1 |
| MDM2.Bf.202-13.M.E8 (Eprimer) | 5'-CGGGGnCCGCTGC-3' (n: exciton (thiazole orange) labelled Thymine) | 6 | 100 | 1 |

TABLE 4

(Premix)

| | |
|---|---|
| Distilled water | 21.05 µL |
| 50× ROX (product name, Roche Ltd.) | 1.28 µL |
| 2× buffer | 31.90 µL |
| Primer mix | 4.47 µL |
| DNA sample (375 copies/reaction or 750 copies/reaction) | 2.55 µL |
| Total | 61.25 µL |

(3) Analysis

The premix and enzyme (polymerase) were mixed so as to achieve the composition shown in the following Table 5, thereby preparing a reaction solution.

TABLE 5

| (Reaction solution) | |
|---|---|
| Premix | 61.25 µL |
| Aac polymerase (30U) | 2.55 µL |
| Total | 63.80 µL |

Next, 14.5 µL of each of two kinds of reaction solutions was collected and each reaction solution was introduced into a chip (QuantStudio 3D Digital PCR Chip, product of Applied Biosystems), thereby fractionating into about twenty-thousand fractions. After the fractionation, the chip was disposed on a heat block at 60° C., and the target sequence and its complementary sequence in the template DNA was amplified for 30 minutes with respect to each fraction. After the amplification, the fluorescence signal of each fraction was detected using an optical measurement apparatus (QuantStudio 3D Digital PCR Instrument, product of Applied Biosystems). With respect to the obtained data, the number of fractions of the reference dye (ROX)-positive and E primer-derived fluorescence signal-positive were counted using analysis software (QuantStudio 3D Analysis Suite, product of Applied Biosystems), thereby calculating the measured value of the number of the template DNA copies contained in the reaction solution. By measuring the ROX with respect to each fraction, it was checked whether each tiny dented reaction vessel in a chip is filled with a reaction reagent properly (whether a fraction is formed properly).

As the analysis method of Comparative Example 1, 14.5 µL of each of two kinds of reaction solutions was collected for 3 times of reaction (14.5 µL×3), and each reaction solution was introduced into a PCR tube without conducting fractionation. Subsequently, by detecting a signal over time under the condition at 60° C. in each of the tubes using a thermal cycler (STEPONE® Real-Time PCR System, product of Applied Biosystems), the detection time from the time of starting the reaction to the time of obtaining a designated signal intensity was measured.

Figure 2:
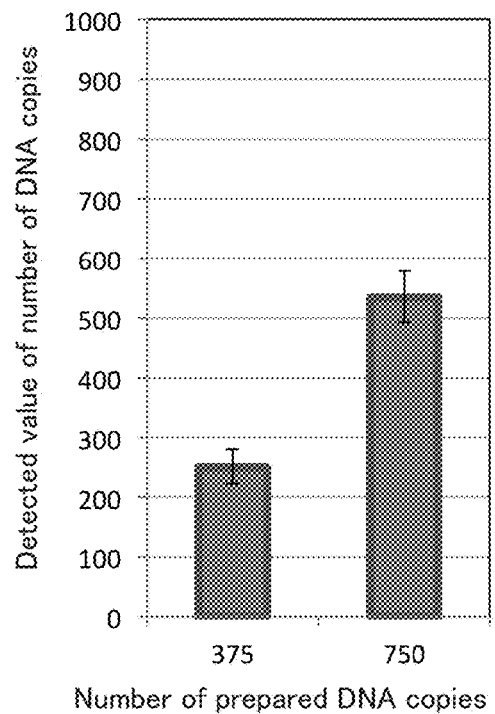
FIG. 2A is a graph showing the measured value of the number of DNA copies in the case where the number of prepared template DNA copies is 375 or 750 in Example 1.
FIG. 2B is a graph showing the detection time in the case where the number of prepared template DNA copies is 375 or 750 in Comparative Example 1
Figure 2:
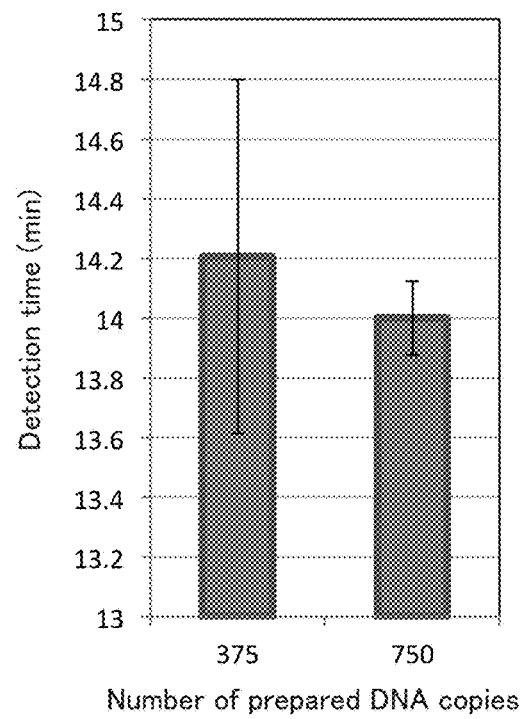

The results are shown in FIGS. 2A and 2B. FIG. 2A is a graph showing the measured value of the number of template DNA copies in the case where the number of prepared template DNA copies is 375 or 750 copies/reaction in the analysis method in Example 1. FIG. 2B is a graph showing the detection time in the case where the number of prepared template DNA copies is 375 or 750 in the analysis method of Comparative Example 1. In FIG. 2A, the vertical axis indicates the measured value of the number of template DNA copies. In FIG. 2B, the vertical axis indicates the detection time. In each of FIGS. 2A and 2B, the bars indicate, from the left side, the result of the reaction system in the case where the number of prepared template DNA copies is 375 copies/reaction and the result of the reaction system in the case where the number of prepared template DNA copies is 750 copies/reaction. As shown in FIG. 2B, in the analysis method of Comparative Example 1, the detection time was not significantly changed even by doubling the number of prepared template DNA copies in the reaction solution. On the other hand, as shown in FIG. 2A, in the analysis method of Example 1, the measured value of the number of template DNA copies was increased by 2.13 times by doubling the number of prepared template DNA copies, which shows the correlation between the measured value of the number of template DNA copies and the number of prepared template DNA copies. These results show that the method for analyzing a template nucleic acid of the present invention allows a template nucleic acid to be analyzed accurately, for example, even in the case where the concentration of a target template nucleic acid is low such as 1000 copies or less and the number of copies cannot be compared by the analysis method of Comparative Example 1 having no fractionation step.

Example 2

The fact that a target nucleic acid can be analyzed accurately by the method for analyzing a target substance of the present invention using a plurality of probes was confirmed.

(1) DNA Sample and Detection Probe

The case nucleic acid model and the control nucleic acid model shown in the following Table 6 were prepared as DNA samples, and the thiazole orange-labeled Eprobe (TO probe) for case nucleic acid model detection and the thiazole pink-labeled Eprobe (TP probe) for control nucleic acid model detection shown in the following Table 6 were prepared as detection probes (fluorogenic probes).

TABLE 6

| Name | Base sequence | SEQ ID NO. |
|---|---|---|
| Case nucleic acid model | 5'-CTACGCCACCAGCT-3' | 7 |
| Control nucleic acid model | 5'-GAGAAAGAGAAAGATACACA-3' | 8 |
| Thiazole orange-labeled Eprobe (TO) for case nucleic acid model detection | 5'-AGCTGGTGGCGnAG-3' (n: thiazole orange-labele thymine) | 9 |
| Thaizole pink-labeled Eprobe (TP) for control nucleic acid model detection | 5'-TGTGTATCnTTCTCTTTCTC-3' (n: thiazole pink-labeled thymine) | 10 |

(2) Experimental Method

The probes were added to RNase Free Water so as to achieve 0.25 µmol/L TO probe and 0.25 µmol/L TP probe, thereby preparing a TO/TP probe mixture. Then, the case nucleic acid model and the control nucleic acid model were added to RNase Free Water so as to achieve the case/control nucleic acid model concentration ratios shown in the following Table 7, thereby preparing six kinds of model samples. Then, 50 µL of the TO/TP probe mixture and 50 µL of each of the model samples were mixed at normal temperature (25° C.). After the mixing, using a fluorescence spectrometer (product of JASCO), the fluorescence intensity (TO fluorescence intensity) at the wavelength of 510 nm in the case where the mixture was excited with the excitation light having a wavelength of 488 nm and the fluorescence intensity (TP fluorescence intensity) at the wavelength of 600 nm in the case where the mixture was excited with the excitation light having a wavelength of 570 nm were measured. For standardizing the measured fluorescence intensity, the case/control nucleic acid models each having a ratio between the final concentration of the case nucleic acid model (Ca) and the final concentration of the control nucleic acid model (Co) (Ca/Co) of 0 µmol/L/0 µmol/L, 0.25 µmol/L/0 µmol/L, or 0 µmol/L/0.25 µmol/L were prepared, and the TO fluorescence intensity and the TP fluorescence intensity were measured. With respect to each model sample, the TO fluorescence variation rate and the TP fluorescence variation rate were calculated based on the following equations (1) and (2).

TABLE 7

| Model sample No. | 1 | 2 | 3 | 4 | 5 |
|---|---|---|---|---|---|
| Case nucleic acid model concentration [µmol/L] | 0.125 | 0.063 | 0.063 | 0.038 | 0.188 |
| Control nucleic acid model concentration [µmol/L] | 0.125 | 0.188 | 0.063 | 0.113 | 0.063 |
| Case/control nucleic acid model concentration ratio | 1.000 | 0.333 | 1.000 | 0.333 | 3.000 |

$$\text{TO fluorescence variation rate} = (S_{TO} - TO_{min}) / (TO_{max} - TO_{min}) \quad (1)$$

$S_{TO}$: TO fluorescence intensity of model sample
$TO_{min}$: TO fluorescence intensity of case/control nucleic acid model having Ca/Co ratio of 0 µmol/L/0 µmol/L
$TO_{max}$: TO fluorescence intensity of case/control nucleic acid model having Ca/Co ratio of 0.25 µmol/L/0 µmol/L $$\text{TP fluorescence variation rate} = (S_{TP} - TP_{min}) / (TP_{max} - TP_{min}) \quad (2)$$

Figure 3:
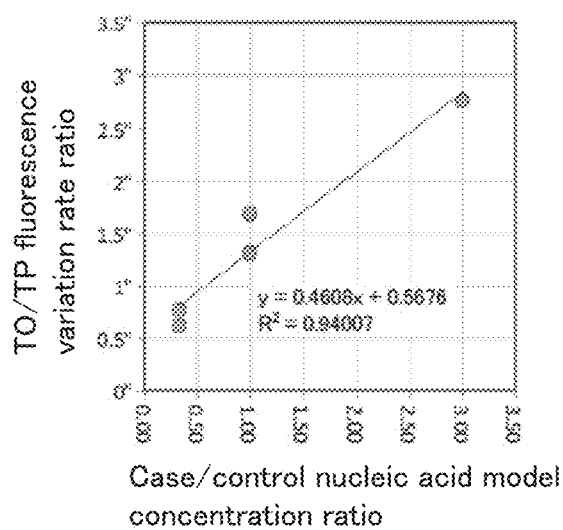
FIG. 3 is a graph showing the comparison between the case/control nucleic acid model concentration ratio and the TO/TP fluorescence variation rate ratio in Example 2.

$S_{TP}$: TP fluorescence intensity of model sample
$TP_{min}$: TP fluorescence intensity of case/control nucleic acid model having Ca/Co ratio of 0 µmol/L/0 µmol/L
$TP_{max}$: TP fluorescence intensity of case/control nucleic acid model having Ca/Co ratio of 0 µmol/L/0.25 µmol/L (3) Results The results are shown in Table 8. Furthermore, FIG. 3 is a graph showing the comparison between the case/control nucleic acid model concentration ratios shown in Table 7 and the TO/TP fluorescence variation rate ratios shown in Table 8. In FIG. 3, the horizontal axis indicates the case/control nucleic acid model concentration ratio, the vertical axis indicates the TO/TP fluorescence variation rate ratio, the straight line and the equations indicate the linear regression equation, and $R^2$ denotes the square value of a correlation coefficient. As shown in FIG. 3, the TO/TP fluorescence variation rate ratio shows a significantly high correlation with the case/control nucleic acid model concentration ratio. These results show that the method for analyzing a target substance of the present invention allows a target nucleic acid to be analyzed accurately.

TABLE 8

| Model sample No. | 1 | 2 | 3 | 4 | 5 |
|---|---|---|---|---|---|
| TO fluorescence variation rate (488 nm) | 0.591 | 0.550 | 0.487 | 0.437 | 0.827 |
| TP fluorescence variation rate (570 nm) | 0.451 | 0.891 | 0.289 | 0.566 | 0.299 |
| TO/TP fluorescence variation rate ratio | 1.313 | 0.617 | 1.683 | 0.771 | 2.765 |

Example 3

The influence of the background signal was checked using the fluorogenic primer or the intercalator as the signal generating substance.

In the case of detecting a single target substance molecule, for obtaining the signal exceeding the detection limit from a single target substance molecule, for example, the amplification reaction is performed longer than the case where many target molecules are present. Hence, using the fluorogenic primer or the intercalator and adopting reverse transcription (RT)-SmartAmp as the amplification method, increase in the background signal in accordance with increase in the amplification time was checked.

TABLE 9

(Primer mix)

| Name | Sequence | SEQ ID NO. | Concentration µmol/L | Amount in reaction solution µL |
|---|---|---|---|---|
| Flu_A_MP1.Tf.183-19.223-14 | TTCCATTGCGAATGCACATTCGAAGCAAC | 11 | 100 | 0.3 |
| Flu_A_MP1.Fr.224-20.n | GCATTCGCGAAATGATAATACCAGATCC | 12 | 100 | 0.59 |
| Flu_A_MP1.Br.195-15 | ACCACTAGATTTCCAG | 13 | 100 | 0.07 |
| Flu_A_MP1.Of.140-19 | ACACTAGTAGAGCCGGGAGA | 14 | 100 | 0.02 |
| Flu_A_MP1.Of.162-20 | CTGGTGTTTATAGCACCCTT | 15 | 100 | 0.02 |
| 50x ROX (product name, product of Roche Ltd) | | | | 0.29 |
| Distilled water | | | | 0.22 |
| Total amount | | | | 1.53 |

(4× reaction buffer #6)
5.6 mmol/L dNTP
80 mmol/L Tris-HCl (pH 8)
40 mmol/L (NH$_4$)$_2$SO$_4$
32 mmol/L MgSO$_4$
0.4% Tween 20
120 mmol/L CH$_3$COOK

TABLE 10

(Reaction solution composition 1)

| Reagent | Amount in reaction solution μL |
|---|---|
| 4× reaction buffer #6 | 3.63 |
| 23 U/μL Aac DNA Polymerase (product of Kabushiki Kaisha DNAFORM) | 1.21 |
| 6 U/μL AMV reverse transcriptase (RT) (product of Fermentus) | 0.17 |
| primer mix | 1.53 |
| Eprimer | 0.16 |
| Distilled water | 6.80 |
| RNA/Easy dilution solution (FluA 0 copies) | 1.00 |
| Total amount | 14.50 |

(Fluorogenic Primer)
E primer FluA_MP1.Br.194-16.E10

```
                                    (SEQ ID NO: 16)
ACCACnAGATTTCCAG
```

(n: thiazole orange-labeled thymine)

TABLE 11

(Reaction solution composition 2)

| Reagent | Amount in reaction solution μL |
|---|---|
| 4× reaction buffer #6 | 3.63 |
| 23 U/μL Aac DNA Polymerase (product of Kabushiki Kaisha DNAFORM) | 1.21 |
| 6 U/μL AMV reverse transcriptase (RT) (product of Fermentus) | 0.17 |
| Primer mix | 1.53 |
| 1/2000-diluted SYBR Green I (product of TAKARA BIO INC.) | 0.29 |
| Distilled water | 6.67 |
| RNA/Easy dilution solution (FluA 0 copies) | 1.00 |
| Total amount | 14.50 |

The primer mix for FluA detection according to the reverse transcription (RT)-SmartAmp was used. The reaction solution was prepared according to the reaction solution composition 1 or the reaction solution composition 2 such that each reaction solution has no target substance (FluA) (n=3 in each solution). Then, each of the reaction solutions was provided to a chip for solution fractionation of a QuantStudio 3D digital PCR system (product of ABI), the reaction solution was reacted at 67° C. for a predetermined time (0, 20, 40, or 60 minutes), and then the reaction solution was cooled to normal temperature. After cooling, with respect to each chip containing the reaction solution, the signal by the fluorogenic primer or the signal by the intercalator (SYBR Green) was quantified using the above-described system.

Figure 4:
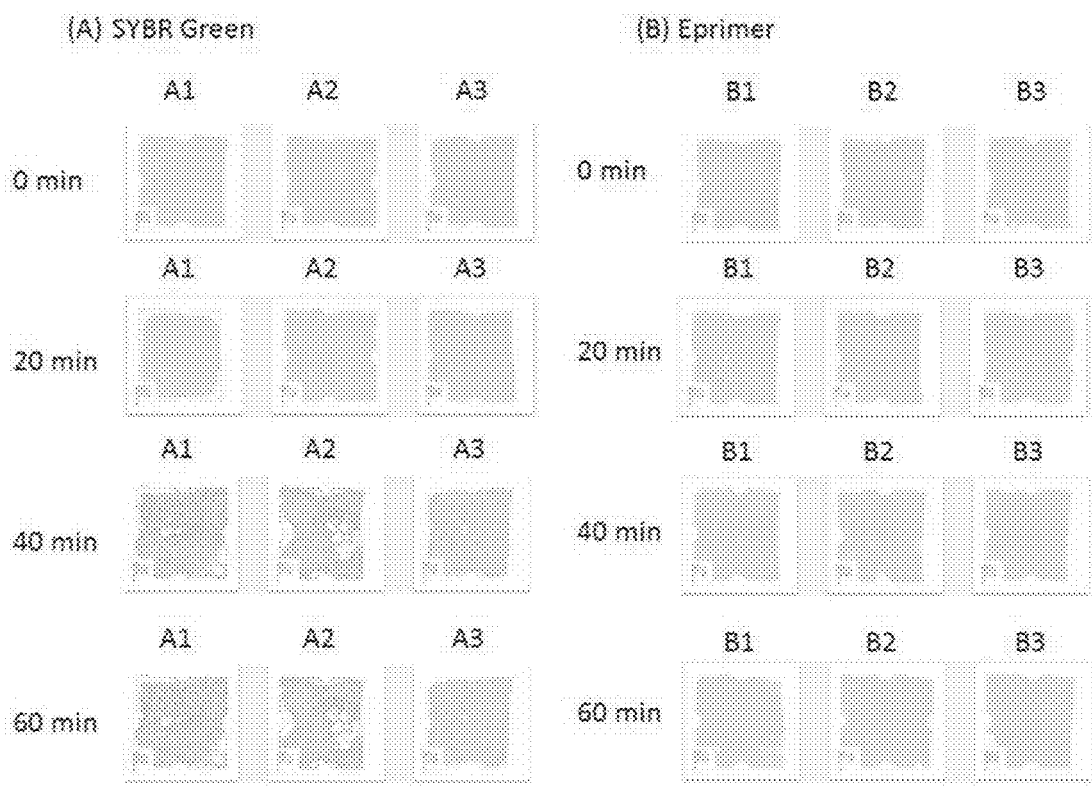
FIGS. 4A and 4B shows images each showing the generation of a signal in Example 3.
Figure 5:
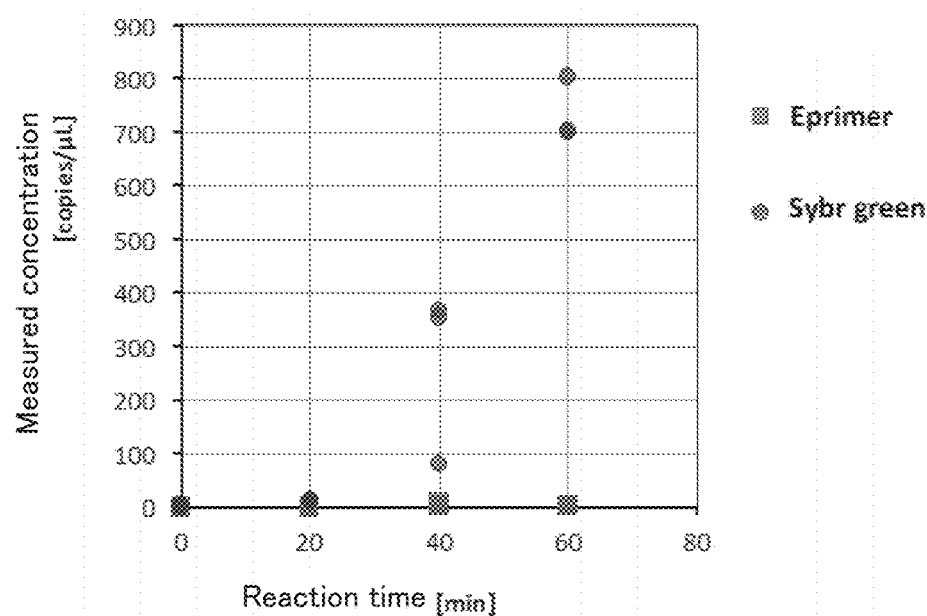
FIG. 5 is a graph showing the measured concentration of a target substance calculated from the fluorescence signal in a reaction solution in Example 3.

The results are shown in FIGS. 4 and 5. FIG. 4 shows images of signals in chips (experiments 1, 2, and 3) over time quantified by the above described system. FIG. 4A shows the results obtained using the intercalator (SYBR Green). A1, A2, and A3 in FIG. 4A each indicate the results of each of the three reaction solutions. FIG. 4B shows the result obtained using the fluorogenic primer (E primer). B1, B2, and B3 in FIG. 4B each indicate the results of each of the three reaction solutions. Note that when the color of the image is darker than the reaction time (0 min), it means that an independent amplification is generated and a signal is generated. FIG. 5 is a graph showing the measured concentration (μL) calculated from the fluorescence of the reaction solution in each reaction time. Each "filled circle (●)" indicates the result obtained using the intercalator (SYBR Green), and each "filled square (□)" indicates the result obtained using the fluorogenic primer (E primer).

As shown in FIG. 4A, in the case of using the intercalator, the color of the image of the reaction time of 40 minutes and the color of the image of the reaction time of 60 minutes were darker than the color of the image of the reaction time 0 minute, whereas the color of the image of the reaction time of 20 minutes was almost the same as the color of the image of the reaction time of 0 minute. Also in FIG. 5 showing the measured results thereof, the measured concentration was increased as the reaction time exceeds 40 minutes whereas the measured concentration was hardly increased at the reaction time of 20 minutes. These results show that, in the case of using the intercalator, for example, by setting the reaction time about 20 minutes, the background can be suppressed sufficiently.

In the case of using the fluorogenic primer, as shown in FIG. 4, even when the amplification reaction time has elapsed, the images were the same as the image of the reaction time of 0 minute, which shows that the fluorescence signal was not generated by nonspecific amplification. Also in the graph of FIG. 5 showing the measured results thereof, even when the amplification reaction time has elapsed, the fluorescence signal was hardly increased, and the measured value never exceeded 10 copies/μL even after the elapse of 60 minutes. These results show that, in the case of using the fluorogenic primer, for example, even when the amplification time for increasing the signal to be generated is elongated, the signal in the background can be suppressed sufficiently.

Example 4

RNA (FluA) was Detected Using the Fluorogenic Primer.

The concentration was measured based on the amplification reaction at 67° C. for a predetermined time (0, 20, or 40 minutes) and the signal measurement in the same manner as in Example 3 except that FluA/RNA (PLoS ONE 2012, 7(1), e30236) of a predetermined number of copies (0, 1500, or 3000 copies) was mixed in the reaction solution (reaction solution composition 1) of Example 3 (n=1). Then, the correction value was obtained by subtracting the measured value of the reaction solution in which the number of copies at the time of starting the reaction was 0 from the measured value of each of the reaction solutions in which the number of copies at the time of starting the reaction was 1500 copies and 3000 copies.

Figure 6:
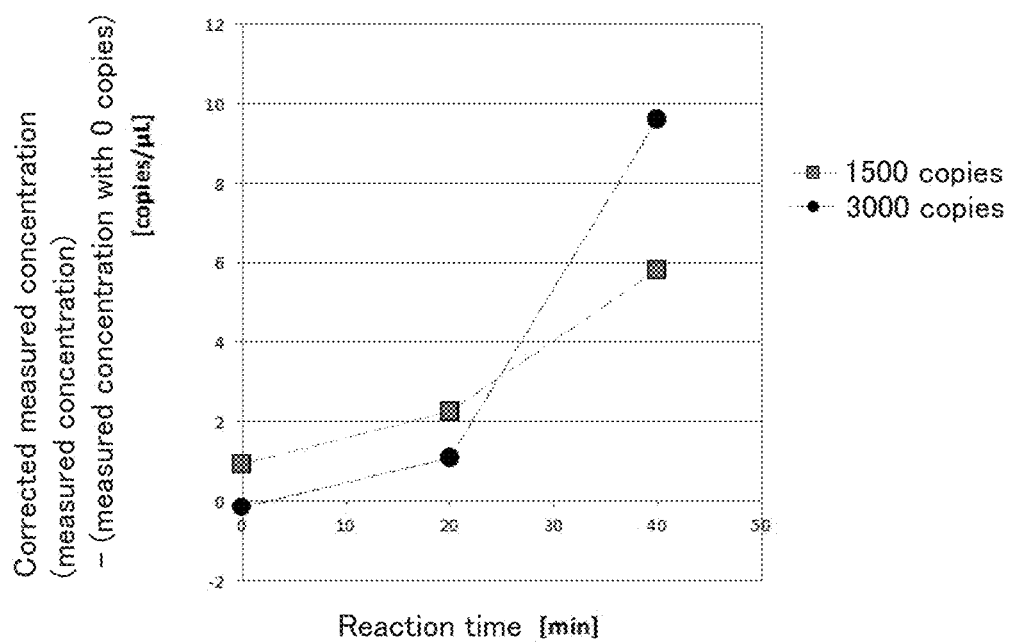
FIG. 6 is a graph showing the measured concentration of a target substance calculated from the fluorescence signal in a reaction solution in Example 4.

The results are shown in FIG. 6. FIG. 6 is a graph showing the corrected measured concentration (copies/μL) calculated from the fluorescence of the reaction solution at each reaction time. The measured value of the reaction solution in which the number of copies was 1500 copies and the measured value of the reaction solution in which the number of copies was 3000 copies at the time of starting the reaction were greatly increased to reach the maximum value at the reaction time of 40 minutes. The measured value of the reaction solution in which the number of copies was 3000 copies at the time of starting the reaction was 1.7 times the measured value of the reaction solution in which the number of copies was 1500 copies at the time of starting the reaction at the reaction time of 40 minutes.

Example 5

RNA (FluA) was Detected Using the Intercalator.

The concentration was measured based on the amplification reaction at 67° C. for a predetermined time (0 or 40 minutes) and the signal measurement in the same manner as in Example 3 except that FluA/RNA (PLoS ONE 2012, 7(1), e30236) of a predetermined number of copies (0 or 3000 copies) was mixed in the reaction solution (reaction solution composition 2) of Example 3 using the intercalator (n=1).

Figure 7:
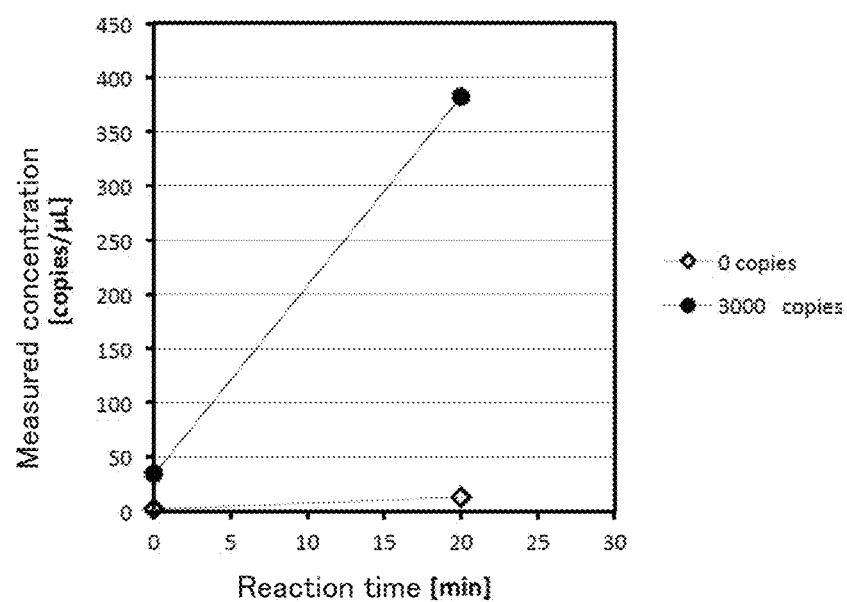
FIG. 7 is a graph showing the measured concentration of a target substance calculated from the fluorescence signal in a reaction solution in Example 5.

The results are shown in FIG. 7. FIG. 7 is a graph showing the measured concentration (copies/μL) calculated from the fluorescence of the reaction solution at each reaction time. The measured value of the reaction solution in which the number of copies was 0 copies at the time of starting the reaction was hardly increased even after 20 minutes from the start of the reaction, whereas the measured value of the reaction solution in which the number of copies was 3000 copies at the time of starting the reaction was greatly increased in 20 minutes from the start of the reaction.

While the present invention has been described above with reference to embodiments and examples, various changes and modifications that may become apparent to those skilled in the art may be made without departing from the scope of the present invention. The entire disclosure of the documents such as the patent documents, academic documents, and the like cited in the specification of the present invention is incorporated herein by reference.

This application claims priority from: Japanese Patent Application No. 2015-169833 filed on Aug. 28, 2015 and Japanese Patent Application No. 2016-096998 filed on May 13, 2016. The entire disclosure of these Japanese Patent Applications is incorporated herein by reference.

INDUSTRIAL APPLICABILITY

According to the present invention, a template nucleic acid can be analyzed accurately.

The invention claimed is:

1. A method for analyzing a template nucleic acid, comprising:

fractionating a sample comprising a template nucleic acid into a plurality of template nucleic acid fractions;

amplifying a target sequence and its complementary sequence in the template nucleic acid with respect to each of the plurality of template nucleic acid fractions in the presence of a nucleic acid amplification reagent;

detecting generation or quenching of a signal that shows an amplification of the target sequence or the complementary sequence with respect to each of the plurality of template nucleic acid fractions after the amplification; and discriminating a template nucleic acid fraction in which the generation or quenching of the signal that shows the amplification has been detected among the plurality of template nucleic acid fractions as an amplified fraction in which the target sequence or the complementary sequence has been amplified, wherein the nucleic acid amplification reagent comprises:

a primer set that amplifies the target sequence and the complementary sequence; and a signal generating substance that generates or quenches the signal in response to the amplification, wherein the signal generating substance is selected from the group consisting of a substance that generates the signal in a state where it is bound sequence-dependently and quenches the signal in a state where it is not bound; and a substance that quenches the signal in the state where it is bound sequence-dependently and generates the signal in the state where it is not bound, generating and quenching of the signal by the signal generating substance are reversible;

the signal generating substance includes a fluorogenic probe, which comprises at least two fluorescent atomic groups per molecule that exhibit an exciton effect, the fluorogenic probe is selected from the group consisting of a probe that generates the signal in a state where it is bound to the target and quenches the signal in a state where it is dissociated from the target and a probe that quenches the signal in the state where it is bound to the target and generates the signal in the state where it is dissociated from the target, the primer set optionally comprises a fluorogenic primer, which comprises at least two fluorescent atomic groups per molecule that exhibit an exciton effect, the fluorogenic primer is selected from the group consisting of a primer that generates the signal in the state where it is bound to the target and quenches the signal in the state where it is dissociated from the target and a primer that quenches the signal in the state where it is bound to the target and generates the signal in the state where it is dissociated from the target, the at least two fluorescent atomic groups that exhibit the exciton effect in the fluorogenic probe or the primer are included in a base, the base comprises a structure represented by the following formulae (16), (16b), (17), or (17b):

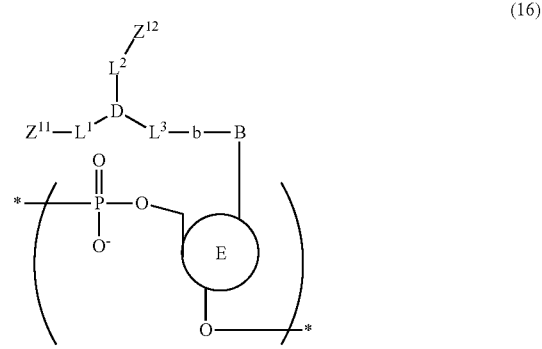

(16)

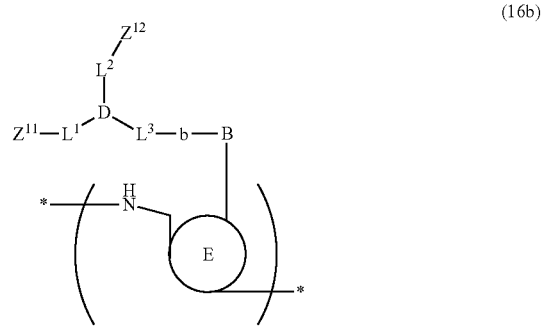

(16b)

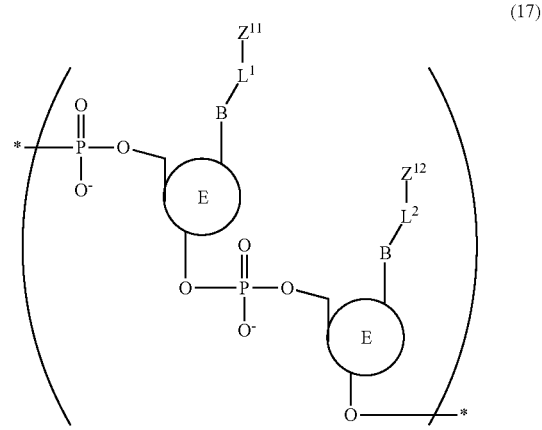

(17)

-continued

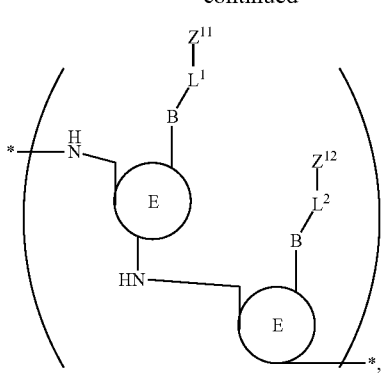

(17b)

wherein in the formulae (16), (16b), (17), and (17b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each an atomic group exhibiting fluorescence, and may be identical to or different from each other, $L^1$, $L^2$, and $L^3$ are each a linker (a linking atom or an atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, where R is a hydrogen atom, an alkyl group, or an arbitrary substituent, and b is a single bond, a double bond, or a triple bond, or alternatively, in the formulae (16) and (16b), $L^1$ and $L^2$ are each a linker, $L^3$, D, and b may not be present, and $L^1$ and $L^2$ may be bonded directly to B, provided that:

in the formulae (16), and (17), E is an atomic group described in the item (i), and at least one 0 atom in a phosphoric acid linkage may be substituted with an S atom;

in the formulae (16b), and (17b), E is an atomic group described in the item (ii); and in the formulae (17) and (17b), the respective Bs may be identical to or different from each other, and the respective Es may be identical to or different from each other.

2. The method for analyzing the template nucleic acid according to claim 1, further comprising:
recovering the amplified fraction from the plurality of template nucleic acid fractions after the discriminating.

3. The method for analyzing the template nucleic acid according to claim 2, further comprising:
amplifying the target sequence and the complementary sequence in the template nucleic acid with respect to the amplified fraction after the discriminating, wherein the amplifying is a second amplifying.

4. The method for analyzing the template nucleic acid according to claim 1, wherein
the detecting is conducted by a melting curve analysis.

5. The method for analyzing the template nucleic acid according to claim 1, further comprising:
conducting an analysis by a melting curve analysis after the detecting.

6. The method for analyzing the template nucleic acid according to claim 1, wherein
the sample comprising the template nucleic acid comprises the nucleic acid amplification reagent, and
in the fractionating, the sample comprising the template nucleic acid and the nucleic acid amplification reagent is fractionated into the plurality of template nucleic acid fractions.

7. The method for analyzing the template nucleic acid according to claim 1, wherein
the fractionating causes each of the plurality of template nucleic acid fractions to contain the nucleic acid amplification reagent.

8. The method for analyzing the template nucleic acid according to claim 1, wherein
the fractionating comprises forming an emulsion from the sample,
the template nucleic acid fraction is a drop of the sample dispersed in the emulsion, and
the detecting is detecting the generation or quenching of the signal with respect to the drop in the emulsion.

9. The method for analyzing the template nucleic acid according to claim 8, wherein
in the detecting,
the emulsion is caused to pass through a flow channel, and
the generation or quenching of the signal is detected with respect to the drop at a predetermined site of the flow channel when the drop in the emulsion passes through the flow channel.

10. The method for analyzing the template nucleic acid according to claim 1, wherein
the fractionating is fractionating the sample into the plurality of template nucleic acid fractions by dispensing the sample to a chip provided with a plurality of template nucleic acid fraction formation portions on its surface.

11. The method for analyzing the template nucleic acid according to claim 10, wherein
in the chip, a surface of the template nucleic acid fraction formation portion is hydrophilic and a surface of a region excluding the template nucleic acid fraction formation portion is hydrophobic, and
the fractionating is fractionating the sample into the plurality of template nucleic acid fractions by applying the sample to the surface of the chip to separate the sample into the template nucleic acid fraction formation portions.

12. The method for analyzing the template nucleic acid according to claim 10, wherein
in the chip, the template nucleic acid fraction formation portion is a dent of the surface of the chip,
the region excluding the template nucleic acid fraction formation portion is a non-dent, and the fractionating is fractionating the sample by introducing the sample into the dents on the surface of the chip.

13. The method for analyzing the template nucleic acid according to claim 10, wherein in the chip, the template nucleic acid fraction formation portion is a dent of the surface of the chip, and an inner surface of the template nucleic acid fraction formation portion is hydrophilic, and the region excluding the template nucleic acid fraction formation portion is a non-dent, and a surface of the region excluding the template nucleic acid fraction formation portion is hydrophobic.

14. The method for analyzing the template nucleic acid according to claim 10, wherein the nucleic acid amplification reagent is arranged in the template nucleic acid fraction formation portion of the chip, and the fractionating causes the template nucleic acid fraction to contain the nucleic acid amplification reagent in the template nucleic acid fraction formation portion of the chip.

15. The method for analyzing the template nucleic acid according to claim 10, wherein the detecting is obtaining an image of the plurality of template nucleic acid fractions on at least one chip, and the discriminating is discriminating the template nucleic acid fraction on the chip in which the generation or quenching of a signal has been detected in the image as the amplified fraction.

16. The method for analyzing the template nucleic acid according to claim 1, wherein the fractionating is fractionating the sample into the plurality of template nucleic acid fractions by dropping the sample.

17. The method for analyzing the template nucleic acid according to claim 1, wherein in the fractionating, an average volume of the plurality of template nucleic acid fractions is 0.0001 to 5000 nL.

* * * * *